US010799600B1

(12) United States Patent
Yeoman et al.

(10) Patent No.: US 10,799,600 B1
(45) Date of Patent: Oct. 13, 2020

(54) TARGETED NANOPARTICLES

(71) Applicant: nanoDERM Sciences, Inc., Derwood, MD (US)

(72) Inventors: Roy R. Yeoman, Burke, VA (US); Richard A. Winchurch, Lutherville, MD (US)

(73) Assignee: NANODERM SCIENCES, INC., Derwood, MD (US)

( * ) Notice: Subject to any disclaimer, the term of this patent is extended or adjusted under 35 U.S.C. 154(b) by 0 days.

(21) Appl. No.: 16/383,940

(22) Filed: Apr. 15, 2019

Related U.S. Application Data

(63) Continuation of application No. 15/627,530, filed on Jun. 20, 2017, now abandoned, which is a continuation-in-part of application No. 14/847,213, filed on Sep. 8, 2015, now Pat. No. 9,694,085, which is a continuation of application No. 13/943,074, filed on Jul. 16, 2013, now Pat. No. 9,161,962, and a continuation-in-part of application No. 13/286,320, filed on Nov. 1, 2011, now Pat. No. 8,821,933.

(60) Provisional application No. 61/672,177, filed on Jul. 16, 2012, provisional application No. 61/344,872, filed on Nov. 1, 2010.

(51) Int. Cl.

| | |
|---|---|
| *A61K 47/69* | (2017.01) |
| *A61K 47/61* | (2017.01) |
| *A61K 39/44* | (2006.01) |
| *A61K 38/12* | (2006.01) |
| *C08G 65/332* | (2006.01) |
| *A61K 49/00* | (2006.01) |
| *A61K 45/06* | (2006.01) |
| *A61K 31/713* | (2006.01) |
| *A61K 9/06* | (2006.01) |
| *C08L 63/00* | (2006.01) |
| *C08L 5/02* | (2006.01) |
| *C08J 3/075* | (2006.01) |
| *C08B 37/02* | (2006.01) |
| *B82Y 5/00* | (2011.01) |
| *A61K 47/36* | (2006.01) |
| *C08L 5/00* | (2006.01) |
| *A61K 47/58* | (2017.01) |
| *A61K 47/68* | (2017.01) |
| *A61K 31/196* | (2006.01) |
| *A61K 31/405* | (2006.01) |
| *A61K 31/616* | (2006.01) |
| *C07K 16/28* | (2006.01) |
| *A61K 31/58* | (2006.01) |
| *A61K 31/192* | (2006.01) |

(52) U.S. Cl.
CPC ........... *A61K 47/6931* (2017.08); *A61K 9/06* (2013.01); *A61K 31/192* (2013.01); *A61K 31/196* (2013.01); *A61K 31/405* (2013.01); *A61K 31/58* (2013.01); *A61K 31/616* (2013.01); *A61K 31/713* (2013.01); *A61K 38/12* (2013.01); *A61K 39/44* (2013.01); *A61K 45/06* (2013.01); *A61K 47/36* (2013.01); *A61K 47/58* (2017.08); *A61K 47/61* (2017.08); *A61K 47/6851* (2017.08); *A61K 47/6933* (2017.08); *A61K 47/6935* (2017.08); *A61K 47/6939* (2017.08); *A61K 49/0017* (2013.01); *B82Y 5/00* (2013.01); *C07K 16/2863* (2013.01); *C08B 37/0021* (2013.01); *C08G 65/3322* (2013.01); *C08J 3/075* (2013.01); *C08L 5/00* (2013.01); *C08L 5/02* (2013.01); *C08L 63/00* (2013.01); *C08J 2305/02* (2013.01); *Y10T 428/2982* (2015.01)

(58) Field of Classification Search
CPC ......... A61K 9/516; A61K 45/06; A61K 31/71
USPC ................... 424/190.1, 422; 600/8
See application file for complete search history.

(56) References Cited

U.S. PATENT DOCUMENTS

| | | | |
|---|---|---|---|
| 6,696,089 B2 | 2/2004 | Kabanov et al. | |
| 2004/0028694 A1* | 2/2004 | Young | A61K 9/5169 424/190.1 |
| 2004/0247683 A1 | 12/2004 | Popescu et al. | |
| 2005/0053590 A1 | 3/2005 | Meininger | |
| 2005/0249721 A1 | 11/2005 | Houston | |
| 2007/0116772 A1* | 5/2007 | Sung | A61K 47/6931 424/489 |
| 2007/0231360 A1* | 10/2007 | Peyman | A61K 9/51 424/422 |
| 2009/0004266 A1* | 1/2009 | Sung | A61K 9/0056 424/456 |
| 2009/0169635 A1 | 7/2009 | Schwarz et al. | |

(Continued)

FOREIGN PATENT DOCUMENTS

WO 9637233 A1 11/1996

OTHER PUBLICATIONS

Ma et al., "Thermally Responsive Injectable Hydrogel Incorporating Methacrylate—Polylactide for Hydrolytic Lability." Biomacromolecules 2010, 11, 1873-1881. (Year: 2010).*

(Continued)

*Primary Examiner* — Walter E Webb
(74) *Attorney, Agent, or Firm* — Bernard G. Pike, Pike IP Law, PLLC

(57) ABSTRACT

The invention in the various aspects provides nanogel compositions that are safe for topical, local, and/or systemic delivery, and which can be targeted to select tissues or cells, including pathogens. In some embodiments, conjugation of antibiotics to the nanogel surface, and in particular antibiotics that disrupt outer membranes of Gram negative bacteria or antibiotics that inhibit cell wall synthesis, provide for highly effective targeting and killing of bacterial pathogens, including drug-resistant bacteria.

6 Claims, 12 Drawing Sheets

(56) References Cited

U.S. PATENT DOCUMENTS

2010/0009007 A1   1/2010   Darvari et al.
2012/0107369 A1   5/2012   Yeoman, III et al.

OTHER PUBLICATIONS

Vauthier et al., "Methods for the Preparation and Manufacture of Polymeric Nanoparticles." Pharmaceutical Research, vol. 26, No. 5, May 2009; 1025-1058 (Year: 2009).*

Kim et al., "Temperature-responsive and degradable hyaluronic acid/Pluronic composite hydrogels for controlled release of human growth hormone." Journal of Controlled Release 80 (2002); 69-77.

Raemdonck et al., "Advanced nanogel engineering for drug delivery." Soft Matter 2009:5; 707-715.

Sharma, A. et al., "Toxicological considerations when creating nanoparticle based drugs and drug delivery systems" Jan. 2012, vol. 8, No. 1, pp. 47-69.

Jain, A. et al., "Design and development of ligand-appended polysaccaridic nanoparticles for the delivery of oxaliplatin in colorectal cancer." Nanomedicine: Nanotechnology, Nanotechnology, Biology and Medicine, 2010, vol. 6, pp. 179-190.

Davis, S. S. et al., "Polymers in drug delivery." Current Opinion in Colloid & Interface Science, 1996, vol. 1, pp. 660-666.

Mudshinge, S. R. et al., "Nanoparticles: emerging carriers for drug delivery." Saudi Pharmaceutical Journal, 2011, vol. 19, pp. 129-141.

D1: Lin, C. et al., "Thermosensitive in situ-forming dextran-pluronic hydrogels through Michael addition." Mat. Sci. Eng. C, 2010, vol. 30, pp. 1236-1244.

Ae Jung Huh et al., "Nanoantibiotics": A new paradigm for treating infectious diseases using nanomaterials in the antibiotics resistant era, Journal of Controlled Release, vol. 156, No. 2, Jun. 29, 2011, pp. 128-145, XP028112005, ISSN: 0168-3659, DOI: 10.1016/J.JCONREL.2011.07.002.

Extended European Search Report dated Feb. 26, 2016 for corresponding European application No. 13820121.5-1453/2872120; PCT/US20/13050647.

\* cited by examiner

FIGURE 4

| Property | Monomer | Structure |
|---|---|---|
| Hydrophobic Solubilization/plasticization modifiers | 4-aminosalicylic acid methacrylate | 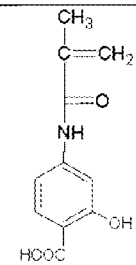 |
| | Styrene | |
| | Stearyl methacrylate | |
| | Methyl methacrylate | |
| | Cyclohexyl methacrylate | |
| | Ethylene glycol phenyl ether methacrylate | |
| | Poly(propylene glycol) methacrylate | |
| | Poly(propylene glycol) 4-nonylphenyl ether acrylate | |

| | | |
|---|---|---|
| Hydrophilic components | Poly(ethylene glycol) methacrylate |  |
| | Acrylamide |  |
| Hydrophilic-Muco-adhesive components | Acrylic acid |  |
| | N-vinylpyrrolidinone |  |
| Thermogelling components | N-isopropylacrylamide (NIPAM) |  |
| | Vinylcaprolactam (VCM) |  |
| | 2-(Diethylamino)ethyl methacrylate |  |

TARGETED NANOPARTICLES

RELATED APPLICATIONS

This application is a continuation-in-part of U.S. application Ser. No. 14/847,213 filed Sep. 8, 2015, which is a continuation of U.S. application Ser. No. 13/943,074 filed Jul. 16, 2013 (now U.S. Pat. No. 9,161,962), which claims the benefit of U.S. Provisional Application No. 61/672,177 filed Jul. 16, 2012. The entire disclosures of the related applications are hereby incorporated by reference in their entireties.

TECHNICAL FIELD

The invention is related to targeted nanoparticles or nanogels. In various embodiments, the invention is related to nanogels functionalized with pathogen-targeting agents or other ligands for targeting select tissue or cells. The nanogels may encapsulate active agents or diagnostic agents, and may be prepared from safe, biodegradable, and/or thermally responsive materials.

BACKGROUND

According to the Centers for Disease Control and Prevention (CDC), each year in the US alone more than 2 million people acquire hospital-acquired infections (HAI) of which almost 100,000 die. Estimated costs associated with HAI in the US are as high as $30 billion annually. Serious bacterial infections such as HAI are often caused by drug-resistant bacterial strains.

Antibacterial resistance generally occurs in three ways: by natural resistance in certain types of bacteria, by genetic mutation, or by one species acquiring resistance from another. Resistance can build up over time, and can result from misuse of antibiotics. Resistant microbes become increasingly difficult to treat, requiring alternative medications or higher doses, both of which may be more costly or more toxic. Microbes which are resistant to multiple antimicrobials are called multidrug resistant (MDR). Antimicrobial resistance is an increasingly problematic issue that leads to millions of deaths every year. Some infections are considered completely untreatable due to resistance.

The rising trend in drug resistance can be attributed to three primary activities: use of antibiotics in the human population, use of antibiotics in the animal population, and the spread of resistant strains between human or non-human sources. Any use of antibiotics can increase selective pressure in a population of bacteria, causing vulnerable bacteria to die thereby increasing the relative numbers of resistant bacteria and allowing for further growth. As resistance to antibiotics becomes more common there is greater need for alternative treatments. Calls for new antibiotic therapies have been issued, but there is continuing decline in the number of approved drugs. The potential crisis at hand is the result of a marked decrease in industry R&D, which has been continually drawn to the search for "blockbuster" drugs for treating chronic illness or cancer, rather than new anti-infective agents.

There are four primary mechanisms by which microorganisms exhibit resistance to antimicrobials. The first is by drug inactivation or modification. For example, some penicillin-resistant bacteria are able to enzymatically deactivate penicillin G through the production of β-lactamases. Alternatively, the protective enzymes produced by the bacterial cell will add an acetyl or phosphate group to a specific site on the antibiotic, which will reduce its ability to bind to bacterial ribosomes and disrupt protein synthesis. A second mechanism is by alteration of a target site, for example, alteration of PBP (the binding target site of penicillins) in MRSA and other penicillin-resistant bacteria, Another protective mechanism found among bacterial species is ribosomal protection proteins. These proteins protect the bacterial cell from antibiotics that target the cell's ribosomes to inhibit protein synthesis. The mechanism involves binding of the ribosomal protection proteins to the ribosomes of the bacterial cell, which in turn changes its conformational shape. This allows the ribosomes to continue synthesizing proteins essential to the cell while preventing antibiotics from binding to the ribosome to inhibit protein synthesis. A third mechanism is alteration of a metabolic pathway. For example, some sulfonamide-resistant bacteria do not require para-aminobenzoic acid (PABA), an important precursor for the synthesis of folic acid and nucleic acids in bacteria inhibited by sulfonamides, instead, like mammalian cells, they turn to using preformed folic acid. A fourth mechanism is by reduced drug accumulation, by decreasing drug permeability or increasing active efflux (pumping out) of the drugs across the cell surface. These specialized pumps can be found within the cellular membrane of certain bacterial species and are used to pump antibiotics out of the cell before they are able to do any damage.

A more effective antimicrobial system would target susceptible microorganisms, while reducing systemic and/or toxic exposure to antibiotics, and/or while reducing exposure to beneficial organisms and minimizing, the development of drug-resistant strains of pathogens and opportunists.

In various embodiments, the present invention meets these or other objectives.

SUMMARY

The invention in the various aspects provides nanogel compositions that are safe for topical, local, and/or systemic delivery, and which can be targeted to select tissues or cells, including pathogens. In some embodiments, conjugation of antibiotics to the nanogel surface, and in particular antibiotics that disrupt outer membranes of Gram negative bacteria or antibiotics that inhibit cell wall synthesis, provide for highly effective targeting and killing of bacterial pathogens, including drug-resistant bacteria.

In one aspect, the invention provides nanoparticle compositions that comprise polymyxin B and/or Vancomycin conjugated to the nanoparticle surfaces. Polymyxin B and Vancomycin may be conjugated to the particle surface together, or alternatively in separate nanoparticle batches and then combined. In various embodiments, polymyxin and/or vancomycin antibiotic bound to the nanoparticle surface avoids or reduces unwanted toxicity of the free antibiotic, while increasing bactericidal or bacteriostatic activity. In some embodiments the highly multivalent nature of the antibiotic on the nanoparticle surface can overcome some resistance acquired by the microorganism. Other antibiotics, such as beta lactam antibiotics, can be conjugated to the nanoparticle surface in other embodiments. Additionally, Pseudouridimycin may be conjugated to or retained within the particle. Pseudouridimycin, polymyxin B and/or vancomycin may be conjugated to the nanoparticle surfaces singularly or in any combination.

Various nanoparticle platforms may be used in accordance with the various aspects of the invention. In some embodiments, the nanoparticle composition is a hydrogel. In some embodiments, the nanoparticles are polymeric, and may comprise cross-linked copolymers and/or a polymeric network. In some embodiments, the hydrogel composition comprises polymeric nanoparticles where at least one co-polymer is a polysaccharide, which is either linear or branched, and may be biodegradable by enzymes present in an animal. In some embodiments, the polysaccharide is a glucan, including but not limited to dextran.

Various co-polymers may be selected for formation of the nanogel compositions, including but not limited to polyvinyl alcohol, acrylate, polyacrylate, polyepoxide, and poloxamer. In these and other embodiment, a second co-polymer may be selected that comprises both hydrophobic and hydrophilic segments, which can provide a micellar property to the nanogel compositions. In some embodiments, the second co-polymer is a poloxamer. For example, in some embodiments, the nanogel composition is prepared from a poloxamer having a polypropylene molecular mass in the range of 2,000 to 6,000 g/mol. In other embodiments, the poloxamer has a polypropylene molecular mass of about 1,800 g/mol. The poloxamer may have a polyoxyethylene content of from 30% to 90%, for example. In some embodiments, the poloxamer is PLURONIC F-127, or a poloxamer having similar polypropylene molecular mass and polyoxyethylene content. In still other embodiments, the nanogel comprises PLURONIC F-68.

The properties of the nanogels may be varied by changing the degree of cross-linking, the molecular weight of the polysaccharide and the poloxamer, the block lengths of the poloxamer, and the addition of any other monomers, and/or chemical linking groups, for example. Nanogels may be produced with different mechanical properties including, but not limited to, mechanical solubility, electric charge, partition coefficient, strength, swelling capacity, diffusion, thermal and/or enzymatic degradation, etc. The physico-chemical properties of the dextran-poloxamer hydrogel conjugates may be modified in order to guide the conjugate selectively to the targeted site to increase the efficacy of the targeting agent. The dextran-poloxamer hydrogel synthesis can be optimized per the specific application for controlled drug delivery and duration of prescribed therapy.

The nanogel composition can be prepared by, for example, a miniemulsion polymerization process, such as, but not limited to, a radical polymerization miniemulsion process, or a controlled radical polymerization process such as atom transfer radical polymerization. For example, polysaccharides can be copolymerized with poloxamers in an inverse miniemulsion process. The polysaccharide may be functionalized with polymerizable functional groups and/or other functional groups such as medicaments or targeting agents prior to, during, or after polymerization. Similarly, the poloxamer may be functionalized with polymerizable functional groups and/or other functional groups such as medicaments or targeting agents prior to, during, or after polymerization.

Embodiments of the nanogels may comprise a nominal diameter between 1 nm and 1000 nm. In other embodiments, the nanogels may comprise a nominal diameter between 10 nm and 500 nm. For certain medicinal applications, embodiments of the nanogel may comprise a nominal diameter between 20 nm and 300 nm. In some embodiments, the hydrogel composition comprises nanoparticles in the range of from 20 to 250 nm in average diameter, or in the range of from 20 to 200 nm in average diameter, or in the range of from 50 to 120 run in average diameter. The nanoparticle size is controlled by addition of an emulsifier, when using the miniemulsion polymerization process.

Surface conjugation of ligands to the particles, including but not limited to polymyxin B and Vancomycin can be conducted by esterification, periodate oxidation, bromide activation, or acid-cleavable linking group.

In some aspects, the invention provides methods for making a nanogel composition. For example, the method may comprise cross-linking dextran acrylate and poloxamer diacrylate in an inverse miniemulsion polymerization, and conjugating a ligand to the nanoparticles formed. With the addition of an emulsifier during the cross-linking, nanoparticle size can be controlled, and may be within the range of 20 to 200 nm in average diameter in various embodiments, or in the range of from 20 to 120 nm in average diameter. Desired targeting ligands can be conjugated to the dextran (before or after cross-linking) by esterification, carbonate ester, periodate oxidation, carbamate ester, bromide activation, or acid-cleavable linking group.

In some embodiments, the nanogels incorporate or encapsulate other materials to add functionality to the compositions, including antimicrobial, anti-inflammatory, wound healing, or other biological property.

In some aspects, the invention provides a method for treating or preventing a bacterial infection, comprising, administering the nanogel described herein to a patient in need thereof. In particular, the invention finds use in treating wounds, including deep cavity wounds, hospital acquired infection, battlefield wound, and burns. In some embodiments, the patient has an antibiotic resistant bacterial infection. In some embodiments, the hydrogel is administered topically to the wound or infected region, or alternatively, is administered systemically, such as for patients showing signs or symptoms of sepsis or bacteremia, or at significant risk thereof.

In various embodiments, the nanogel compositions are administered to treat or prevent sepsis, cellulitis and skin abscesses, pneumonia, toxic shock syndrome, and endocarditis. The present invention provides compositions to treat or prevent infection by a variety of bacterial pathogens, including drug-resistant pathogens. Examples of drug-resistant bacteria include: methicillin-resistant *Staphylococcus aureus* (MRSA), vancomycin-resistant *S. aureus* (VRSA), vancomycin-resistant *Enterococcus* (VRE), and multidrug-resistant *A. baumannii* (MRAB).

Routes of administration include topical administration, intravenous administration, or by intramuscular, intraperitoneal, subcutaneous, intra-articular, intrasynovial, intrathecal, oral, or inhalation routes. In other embodiments, compositions are administered to infected eyes, ears, or sinus.

Other ligands can be incorporated into the hydrogel composition, other than antibiotics, to impart other targeting properties, such as targeting of mammalian tissues and cells, including cancer cells.

Other aspects and embodiments of the invention will be apparent from the following detailed description.

DESCRIPTION

Figure 1:
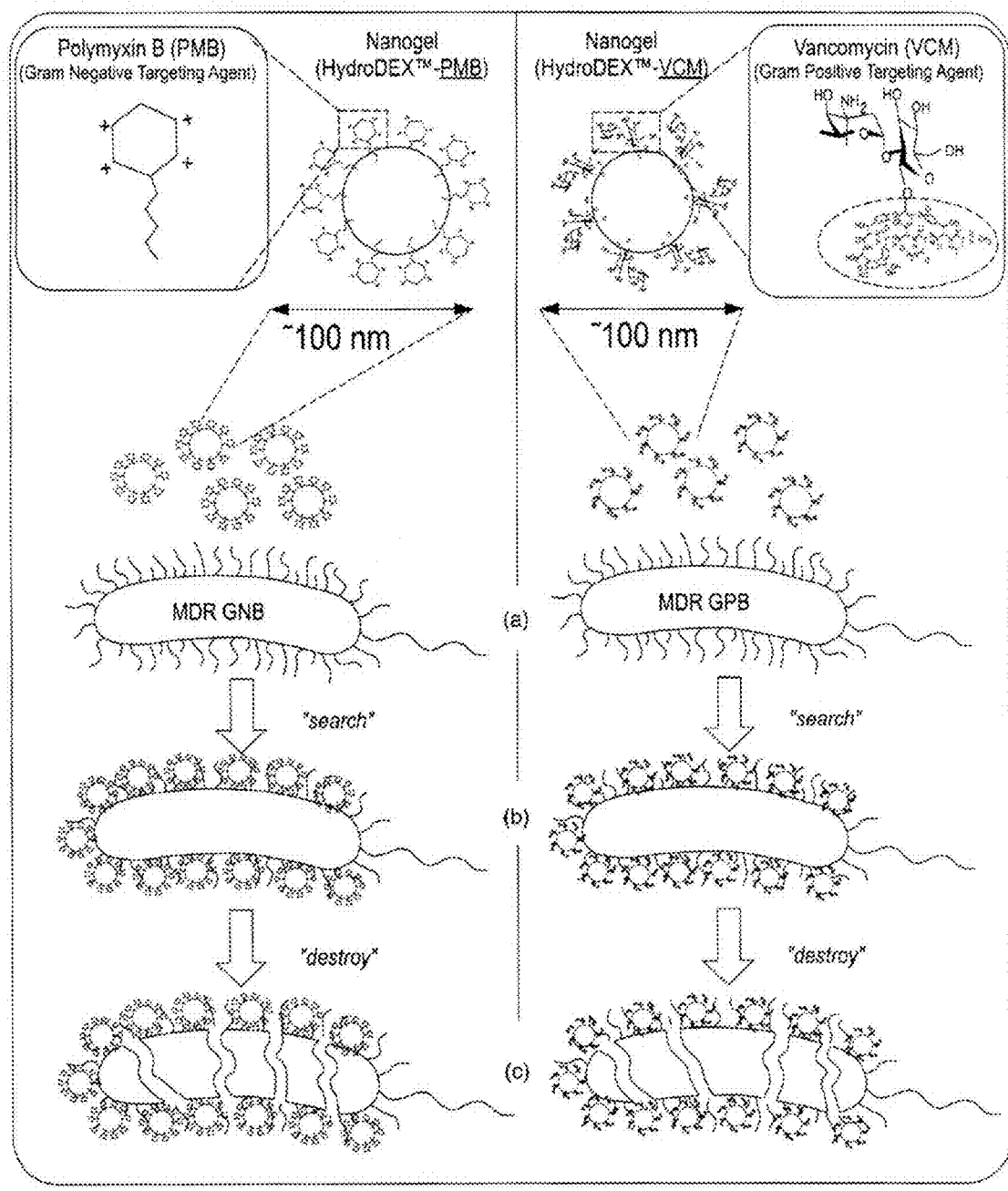
FIG. 1 illustrates embodiments of the invention in which nanogel particles in the 100 nm size range have polymyxin B (left panel) on their surface for targeting, of Gram negative bacteria (including multi-drug resistant Gram negatives, "MDR"), or vancomycin (right panel) for targeting Gram positive bacteria (including multi-drug resistant Gram positives, "MDR").

The invention in the various aspects provides nanogel compositions that are safe for topical, local, and/or systemic delivery, and which can be targeted to select tissues or cells, including pathogens. In some embodiments, conjugation of antibiotics to the nanogel surface, and in particular antibiotics that disrupt outer membranes of Gram negative bacteria or antibiotics that inhibit cell wall synthesis, provide for highly effective targeting and killing of bacterial pathogens, including drug-resistant bacteria.

In one aspect, the invention provides nanoparticle compositions that comprise polymyxin B and/or Vancomycin conjugated to the nanoparticle surfaces. Polymyxin B and Vancomycin may be conjugated to the particle surface together, or alternatively in separate nanoparticle batches and then combined.

Polymyxins are cyclic polypeptide antibiotics. In addition to their bactericidal properties they bind to the lipid A portion of endotoxins and block their biologic properties. Low doses of polymyxin B have been used therapeutically in burn patients to neutralize circulating endotoxin consequent to burn injury. In various embodiments, polymyxin antibiotic bound to the nanoparticle surface avoids or reduces unwanted toxicity of free polymyxin antibiotic, while increasing bactericidal or bacteriostatic activity.

The lipopolysaccharides (LPS) of gram negative bacteria function to provide membrane stabilization, integrity and confer resistance to host defenses. LPS is critical to the proliferation of gram-negative bacteria and disruption, mutation or removal of LPS results in bacterial death. All gram negative bacteria exhibit LPS in their outer membrane. LPS is composed of complex carbohydrates and lipid A. The carbohydrates vary in structure and confer the antigenic properties which distinguish different bacterial strains. The Lipid A is highly conserved across strains and is responsible for many of the pathogenic, immunologic and pyrogenic effects of gram negative bacteria. The ubiquitous nature of LPS makes it an attractive target for treatment of nearly all gram-negative bacterial strains. Lipid A is a critical structural component of LPS. It functions to anchor LPS to the cell membrane and it is structurally bound to the core polysaccharide.

After binding to lipopolysaccharide (LPS) in the outer membrane of gram-negative bacteria, polymyxins disrupt both the outer and inner membranes. The hydrophobic tail is important in causing membrane damage, suggesting a detergent-like mode of action. Removal of the hydrophobic tail of polymyxin B yields polymyxin nonapeptide, which still binds to LPS, but no longer kills the bacterial cell. However, it still detectably increases the permeability of the bacterial cell wall to other antibiotics, indicating it still causes some degree of membrane disorganization.

Polymyxin antibiotics are relatively neurotoxic and nephrotoxic, so are usually used only as a last resort if preferred antibiotics are ineffective or are contraindicated. Typical uses of polymyxin antibiotics are for infections caused by strains of multiple drug-resistant *Pseudomonas aeruginosa* or carbapenemase-producing Enterobacteriaceae. Polymyxins are not absorbed from the gastrointestinal tract, so are often administered intravenously, or are used externally.

Gram-negative bacteria can develop resistance to polymyxins through various modifications of the LPS structure that reduce the binding of polymyxins to LPS. However, in some embodiments the highly multivalent nature of the polymyxin B on the nanoparticle surface, as described herein, can overcome this resistance.

Vancomycin is a glycopeptide antibiotic that acts by inhibiting proper cell wall synthesis in gram-positive bacteria. Due to the different mechanism by which gram-negative bacteria produce their cell walls and the various factors related to entering the outer membrane of gram-negative organisms, vancomycin is not active against most gram-negative bacteria. The large hydrophilic molecule is able to form hydrogen bond interactions with the terminal D-alanyl-D-alanine moieties of the NAM/NAG-peptides. This binding of vancomycin to the D-Ala-D-Ala prevents cell wall synthesis of the long polymers of N-acetylmuramic acid (NAM) and N-acetylglucosamine (NAG) that form the backbone strands of the bacterial cell wall, and it prevents the backbone polymers that do manage to form from cross-linking with each other. Proposed mechanisms of resistance include the sequential mutations resulting in a thicker cell wall and the synthesis of excess amounts of D-ala-D-ala residues.

The glycopeptide antimicrobials are a group of natural product and semisynthetic glycosylated peptides that show antibacterial activity against gram-positive organisms through inhibition of cell-wall synthesis. This is achieved primarily through binding to the d-alanyl-d-alanine terminus of the lipid II bacterial cell-wall precursor, preventing cross-linking of the peptidoglycan layer. Vancomycin is the foundational member of the class, showing both clinical longevity and a still preferential role in the therapy of methicillin-resistant *Staphylococcus aureus* and of susceptible *Enterococcus* spp. Newer lipoglycopeptide derivatives (telavancin, dalbavancin, and oritavancin) were designed in a targeted fashion to increase antibacterial activity, in some cases through secondary mechanisms of action. These glycopeptide antimicrobials and Pseudouridimycin may also be conjugated to the polymers as described.

Vancomycin is highly active when conjugated to the surface of the nanoparticles. In some embodiments, delivery of the vancomycin via the nanoparticle compositions is active even against less susceptible or even resistant gram positive strains, while minimizing toxicity to the host.

In some embodiments, the nanoparticles contain both polymyxin B and vancomycin, thereby providing an effective composition against mixed (gram-positive and gram-negative) infection.

Alternatively or in addition, the hydrogel composition incorporates a glycopeptide antibiotic other than vancomycin, e.g., teicoplanin, on the surface thereof.

In still other embodiments, the hydrogel composition comprises nanoparticles having a beta lactam antibiotic conjugated to their surface. Exemplary beta lactam antibiotics include penicillin or cephalosporin, and derivatives thereof.

Various nanoparticle platforms may be used in accordance with these aspects. In some embodiments, the nanoparticle composition is a hydrogel. In some embodiments, the nanoparticles are polymeric, and may comprise cross-linked copolymers and/or a polymeric network. As used herein, a "hydrogel" is a network of polymer chains that are hydrophilic, sometimes found as a colloidal gel in which water is the dispersion medium. Hydrogels are highly absorbent, and may contain over 90% water, and can be based on natural or synthetic polymeric networks.

In some embodiments, the hydrogel composition comprises polymeric nanoparticles where at least one co-polymer is a polysaccharide, which is either linear or branched. Polysaccharides are long carbohydrate molecules of mono- or di-saccharide units joined together by glycosidic bonds and range in structure from linear to highly branched. Thus, the polysaccharide may be linear or branched, or may be a homopolysaccharide or heteropolysaccharides (e.g., polysaccharides comprising modifications of the repeating unit).

The term "polysaccharide" further includes polysaccharides that have been modified by a reaction of its hydroxyl groups or other group with a compound to a different pendent functional group. Particular embodiments of the polysaccharides are storage polysaccharides and biodegradable polysaccharides. As used herein, "biodegradable polysaccharides" are polysaccharides that are biodegradable by enzymes present in an animal. Additionally, the polysaccharide hydroxyl groups provide a vehicle for producing "tunable" hydrogels.

In some embodiments, the polysaccharide is a glucan. A glucan molecule is a polysaccharide of D-glucose monomers, linked by glycosidic bonds. Glucans include the following: dextran (α-1,6-glucan with α-1,3-branches); glycogen (α-1,4- and α-1,6-glucan); pullulan (α-1,4- and α-1,6-glucan); starch (α-1,4- and α-1,6-glucan); cellulose (β-1,4-glucan); chrysolaminarin (β-1,3-glucan); curdlan (β-1,3-glucan); laminarin (β-1,3- and β-1,6-glucan); lentinan (a strictly purified β-1,6:β-1,3-glucan from *Lentinus edodes*); lichenin (β-1,3- and β-1,4-glucan); oat beta-glucan (β-1,3- and (β-1,4-glucan); pleuran (β-1,3- and β-1,6-glucan isolated from *Pleurotus ostreatus*); and zymosan (β-1,3-glucan). Other biodegradable/biocompatible polysaccharides that may be used for formation of hydrogels include chitosan, which is a linear polysaccharide composed of randomly distributed β-(1-4)-linked D-glucosamine and N-acetyl-D-glucosamine, and hyaluronic acid. Hyaluronic acid is a polymer of disaccharides, themselves composed of D-glucuronic acid and D-N-acetylglucosamine, linked via alternating β-1,4 and β-1,3 glycosidic bonds.

In some embodiments, the polysaccharide is a branched glucan comprising polymeric branches varying in length from 3 to 2000 kilodaltons. In some embodiments, the polysaccharide is dextran. Dextran is a colloidal, hydrophilic, and non-toxic polysaccharide that may be enzymatically degraded in the human body dextranase. Dextran is composed of linear α-1,6-linked D-glucopyranose residues with a low fraction of -1,2, -1,3 and -1,4 linked side chains. Dextrans, as well as other polysaccharides, have a plurality of hydroxyl groups that can be directly reacted to add functional groups to the dextran backbone or may be modified to form reactive end groups which may be used for cross-linking or otherwise functionalizing the hydrogel. For example, the polysaccharide may be functionalized with allyl isocyanate (AI), ethylamine (AE), chloroacetic acid (AC) and/or maleic anhydride (AM). Dextran fulfills many of the ideal characteristic features of a good carrier candidate. It is nontoxic, non-immunogenic and non-antigenic.

Polysaccharides may be linear, branched, or cyclic. Cyclodextrins and Schardinger dextrins are cyclic oligosaccharides formed from starch polysaccharides and are non-reducing D-glucopyranosyl polymers containing six or more units linked by α-D-(1→4) bonds Alpha-, beta-, and gamma-cyclodextrin. Typical cyclodextrins contain a number of glucose monomers ranging from six to eight units in a ring. Natural CDs:

α (alpha)-cyclodextrin: 6-membered sugar ring molecule
β (beta)-cyclodextrin: 7-membered sugar ring molecule
γ (gamma)-cyclodextrin: 8-membered sugar ring molecule are all of these are generally regarded as safe by the FDA, which allows safety assurance of these pro-drugs as new entities.

Although most polysaccharides bear a reducing monosaccharide residue at one end, and are, therefore, reducing polysaccharides, some polysaccharides have nonreducing residues at both ends.

Starch oligosaccharides, which represent the fragments of the original polysaccharide, are composed of α-D-glucopyranosyl units linked by (1→4) and (1→6) bonds. The generic term oligosaccharide is used for saccharides containing fewer than 10 monosaccharide units. The structural analysis of starch fragmentation products is of interest for the characterization of the native starch molecule. Pure oligosaccharides and megalosaccharides are being used in the probing of the amylase subsite, in the elucidation of amylase action, and in the clinical amylase assay. Cyclic oligosaccharides—referred to as cycloamyloses, cyclodextrins or Schardinger dextrins—are formed from starch polysaccharides and are non-reducing D-glucopyranosyl polymers containing six or more units linked by α-D-(1→4) bonds. Cycloamyloses are anomalous structures with interesting physicochemical properties when compared with the linear oligosaccharides Cyclodextrins are composed of 5 or more α-D-glucopyranoside units linked 1→4, as in amylose (a fragment of starch). The 5-membered macrocycle is not natural. Recently, the largest well-characterized cyclodextrin contains 32 1,4-anhydroglucopyranoside units, while as a poorly characterized mixture, at least 150-membered cyclic oligosaccharides are also known.

Because cyclodextrins are hydrophobic inside and hydrophilic outside, they can form complexes with hydrophobic compounds. Thus they can enhance the solubility and bioavailability of such compounds. This is of high interest for pharmaceutical in which hydrophobic compounds shall be delivered. B-cyclodextrin and PED (b-lactam conjugated) as the new nanosized drug carrier device.

Figure 4:
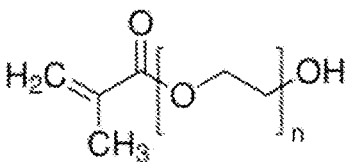
FIG. 4 illustrates monomers and polymers that can be added to the polymerization reaction for achieving various functionalities.
Figure 4:
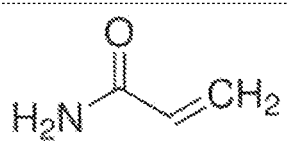
Figure 4:
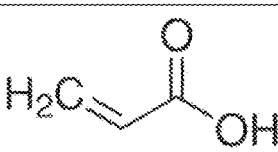
Figure 4:
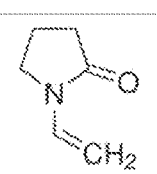
Figure 4:
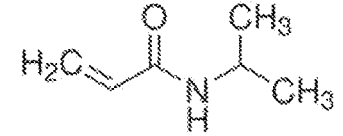
Figure 4:
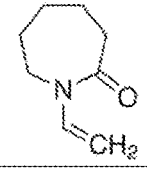
Figure 4:
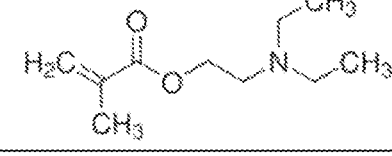

Various co-polymers may be selected for formation of the nanogel compositions, including but not limited to polyvinyl alcohol, acrylate, polyacrylate, polyepoxide, and poloxamer. In these and other embodiment, a second co-polymer may be selected that comprises both hydrophobic and hydrophilic segments, which can provide a micellar property to the nanogel compositions. In some embodiments, the second co-polymer is a poloxamer. Other monomer units that find use as co-polymers are shown in FIG. 4.

Poloxamers are nonionic triblock copolymers composed of a central hydrophobic chain of polyoxypropylene flanked by two hydrophilic chains of polyoxyethylene. Poloxamers are also known by the trade name PLURONICS. Poloxamer solutions can exhibit temperature dependent self-assembly and thermo-gelling behavior. Concentrated aqueous solutions of poloxamers are liquid at low temperature and form a gel at higher temperature in a reversible process. The transitions that occur in these systems depend on the polymer composition (molecular weight and hydrophilic/hydrophobic molar ratio). At low temperatures and concentrations (below the critical micelle temperature and critical micelle concentration) individual block copolymers (unimers) are present in solution. Above these values, aggregation of individual unimers occurs in a process called micellization. This aggregation is driven by the dehydration of the hydrophobic polyoxypropylene block that becomes progressively less soluble as the polymer concentration or temperature increases. The aggregation of several unimers occurs to minimize the interactions of the PPO blocks with the solvent. Thus, the core of the aggregates is made from the insoluble blocks (polyoxypropylene) while the soluble portion (polyoxyethylene) forms the shell of the micelles.

In some embodiments, the nanogel composition is prepared from a poloxamer having a polypropylene molecular mass in the range of 2,000 to 6,000 g/mol. In other embodiments, the poloxamer has a polypropylene molecular mass of about 1,800 g/mol. The poloxamer may have a polyoxyethylene content of from 30% to 90%, for example, about 60%, about 70%, or about 80%. In some embodiments, the poloxamer is PLURONIC F-127, or a poloxamer having similar polypropylene molecular mass and polyoxyethylene content. In still other embodiments, the nanogel comprises. PLURONIC F-68.

In some embodiments, the nanoparticles also exhibit a temperature dependent behavior, either by triggering or accelerating degradation, or by releasing encapsulated therapeutic agent, upon administration to a subject.

In certain embodiments of the polymeric network, the block copolymer of epoxides is a triblock copolymer. The block copolymer may comprise at least one block derived from propylene oxide monomers and at least one block derived from ethylene oxide monomers. In a further embodiment, the block copolymer of epoxides is an ABA triblock copolymer wherein the A block is derived from ethylene oxide monomers and the B block is derived from propylene oxide monomers, such as a poloxamer. Embodiments of the nanogels and nanoparticles may be thermally responsive or degradable at human body temperatures such as in a range of 96° F. to 100° F.

Nanoparticles comprising dextran (polysaccharides) and PLURONIC F127 (poloxamers) may be produced via emulsion (colloidal) process polymerization. Both dextran and PLURONIC F-127 are approved for use by the FDA and a hydrogel formed from these compounds offers a controlled drug delivery platform that is nontoxic, biodegradable, and thermally responsive at normal human body temperatures. For IV applications the poloxamer, PLURONIC F68, can be used for nanoparticle production by the same process. The small molecular weight poloxamer can produce nanoparticles suitable for IV administration.

Additionally, the dextran hydroxyl groups provide a vehicle for producing "tunable" hydrogels. The properties of the nanogels may be varied by changing the degree of cross-linking, the molecular weight of the polysaccharide and the poloxamer, the block lengths of the poloxamer, and the addition of any other monomers, and/or chemical linking groups, for example. Nanogels may be produced with different mechanical properties including, but not limited to, mechanical solubility, electric charge, partition coefficient, strength, swelling capacity, diffusion, thermal and/or enzymatic degradation, etc. The physico-chemical properties of the dextran-poloxamer hydrogel conjugates may be modified in order to guide the conjugate selectively to the targeted site to increase the efficacy of the targeting agent. The dextran-poloxamer hydrogel synthesis can be optimized per the specific application for controlled drug delivery and duration of prescribed therapy, e.g., various dextran-poloxamer varying the ratio of dextran-poloxamer composition.

The nanogel composition can be prepared by, for example, a miniemulsion polymerization process, such as, but not limited to, a radical polymerization miniemulsion process, or a controlled radical polymerization process such as atom transfer radical polymerization. For example, polysaccharides can be copolymerized with poloxamers in an inverse miniemulsion process. The polysaccharide may be functionalized with polymerizable functional groups and/or other functional groups such as medicaments or targeting agents prior to, during, or after polymerization. Similarly, the poloxamer may be functionalized with polymerizable functional groups and/or other functional groups such as medicaments or targeting agents prior to, during, or after polymerization.

In a specific embodiment, both the polysaccharide and poly(epoxide) may be functionalized with cross-linkable double bonds. The cross-linking groups may comprise an ester group. After cross-linking in some embodiments, the linking groups may comprise at least two ester groups. In certain embodiments for biomedical applications, the hydrogel, cross-linked network, and/or the block copolymer comprising a polysaccharide and a poloxamer includes a biocompatible linking group.

While various functional groups can be used to functionalize the co-polymers for cross-linking, in some embodiments the co-polymers are functionalized with meth-acrylate, diacryloyl or dimethacryloyl groups. For example, poloxamer diacrylate may be reacted with a dextran acrylate to form the hydrogel.

The co-polymers (e.g., polysaccharide and poly(epoxide)) may be cross-linked with any polymerization process or appropriate cross-linking reaction including radical polymerizations, emulsion polymerizations, controlled polymerization, UV initiated cross-linking, e-beam curing, or other polymerization process. In one embodiment, the process involves an electron beam curing process during which an aqueous solution of two monomers containing "hard" and "soft" groups on a somewhat flexible backbone undergo a spontaneous reorientation or self-arrangement, for example, "soft" groups tend to approach other "soft" groups and the "hard" groups tend to approach the "hard" groups. The breadth of the distribution of so called hard and soft groups can be modified by incorporating other monomers in the same families.

Miniemulsion polymerization processes are conducted in specially formulated heterophase systems consisting of stable nanodroplets suspended in a continuous phase. The narrowly size distributed nanodroplets of 50 to 500 nm may be prepared by a shearing system containing oil, water, a surfactant, and an osmotic pressure agent which is insoluble in the continuous phase.

Embodiments of the nanogels may comprise a nominal diameter between 1 nm and 1000 nm. In other embodiments, the nanogels may comprise a nominal diameter between 10 nm and 500 nm. For certain medicinal applications, embodiments of the nanogel may comprise a nominal diameter between 20 nm and 300 nm. In some embodiments, the hydrogel composition comprises nanoparticles in the range of from 20 to 250 nm in average diameter, or in the range of from 20 to 200 nm in average diameter, or in the range of from 50 to 120 nm in average diameter. The nanoparticle size is controlled by addition of an emulsifier, when using the miniemulsion polymerization process.

The polymeric network may be cross-linked with chemically or ionizing radiation such as gamma or beta radiation. Other embodiments may result in cross-linking with ionic bonds with polyvalent metals, organic materials having an ionic charge. The cross-linking may be chemical cross-linking.

In some embodiments, using, for example, electron beam cross-linking of a blend of diacryloyl or dimethacryloyl terminated polysaccharide (Dextran) and a diacryloyl or dimethacryloyl terminated triblock copolymer, poly-(ethylene oxide)-b-(propylene oxide)-b-(ethylene oxide), a broad spectrum of hydrogel platforms and porosities can be fashioned.

The copolymer and/or hybrid polymer network may be produced from any desired ratio of polysaccharide to polymer derived from epoxide monomers such as poloxamer. The ratio of polysaccharide to polymer derived from epoxide monomers may be from 1:99 to 99:1. In certain embodiments, the ratio of polysaccharide to polymer derived from epoxide monomers may be from 30:70 to 70:30. Based upon the results of a deswelling study, five hydrogels were produced from the Dextran:poloxamer ratios of 10/90, 30/70, 50/50, 70/30, and 90/10. These hydrogels varied in composition and characterization as indicated with regard to the concentrations of monomers and the degree of crosslinking. The gels were evaluated regarding their physical release (drug delivery capability) and structural properties and the extent of hydration. In some embodiments, the hydrogels comprise cross-linked acrylated dextran and acrylated PLURONIC F-127 at a ratio of from 2:1 to 3:1 wt/wt. In some embodiments, the ratio is about 2.5:1 wt/wt.

The hydrogel comprising a polysaccharide and a poloxamer may be customized by adjusting various properties of the components and process. The degree of cross-linking will affect the properties of the hydrogel such as pore size. For example, in an e-beam cross-linking process, pore size can be adjusted during the irradiation/curing process by adjusting the strength or exposure time of the beam current. As the reaction mixture moves under the e-beam, the three dimensional structures can be controlled to produce a gel with pore sizes related to the absorbed dose. A higher beam current used in a cross-linking process will result in smaller pore sizes while a smaller absorbed dose from the e-beam will result in a larger internal volume of the pore.

As the narrow beam of ionizing, radiation passes through the solution of oriented monomers, the hydrogel is formed containing pores which will attract "hard" and "soft" ions or molecules, which are used as pharmaceuticals. The process will have a significant effect on the rates of diffusion of the pharmaceuticals out of the hydrogel membrane. It may be desirable to increase the elution rate of a given drug from the membrane. Choice of membrane and standard elution rates will provide a hydrogel with a unique handle in product desirability.

The polysaccharide/poly(epoxide) hydrogel, can also be polymerized through other chemical cross-linking methods, for example, peroxide, benzoyl peroxide, t-butyl peroxide, and hydrogen peroxide. These can produce free radicals and crosslink certain unsaturated polymers.

In addition to chemical cross-linking via ultra-violet light, the polysaccharide and poly(epoxide) may also be polymerized using ultra high heat lamps, physical cross-linking, crystallization, hydrogen bonding, etc. Further, high energy electrons can disrupt certain bonds in the polymer molecule initiating crosslinking. Among these are gamma rays (highest energy of all) and radioactive cobalt-60 radioactive source where the energy is related to concentration of $Co^{60}$ in the source.

E-beam cross-linking may be used to produce the polysaccharide/poly(epoxide) hydrogel. Indeed, machine generated high energy electrons (e-beams) may be a preferred production route for the production of a hydrogel in an FDA approved market. This technique offers standardization and reproducibility with large production yield and the environmental advantage that the process does not create chemical waste.

Surface conjugation of ligands to the particles, including but not limited to polymyxin B and Vancomycin can be conducted by esterification, periodate oxidation, bromide activation, or acid-cleavable linking group.

In some aspects, the invention provides methods for making a nanogel composition. For example, the method may comprise cross-linking dexran acrylate and poloxamer diacrylate in an inverse miniemulsion polymerization, and conjugating a ligand to the nanoparticles formed. In some embodiments, acrylated dextran and acrylated PLURONIC F-127 are cross-linked at a ratio of from 2:1 to 3:1 wt/wt. In some embodiments, the ratio is about 2.5:1 wt/wt. With the addition of an emulsifier during the cross-linking, nanoparticle size can be controlled, and may be within the range of 20 to 200 nm in diameter in various embodiments, or in the range of from 20 to 120 nm in diameter. Desired targeting ligands can be conjugated to the dextran (before or after cross-linking) by esterification, carbonate ester, periodate oxidation, carbamate ester, bromide activation, or acid-cleavable linking group.

The hydrogel nanoparticles may encapsulate a therapeutic or diagnostic agent, such as but not limited to glucocorticoid, monoclonal antibody, polynucleotide, peptide agent, an enzyme, hormone, or anti-inflammatory agent. In some embodiments, the therapeutic agent is budesonide, naproxen, aspirin, ketoprofen, ibuprofen, diclofenac, or indomethacin. In some embodiments, the nanoparticles incorporate a diagnostic agent, such as a fluorescently labelled agent (e.g., dye) or a radio labeled biomarker.

In some embodiments, the nanogels incorporate or encapsulate other materials to add functionality to the compositions. For example, in some embodiments, the nanogel incorporates cations (for example, iron, zinc, and/or silver) known to promote wound healing or to be anti-microbial in the case of silver. Specific embodiments of the wound healing agents may comprise a solution comprising zinc ions, silver ions and iron ions. The hydrogel will allow for controlled release of the healing agents of the solution into the wound as well as maintaining the moisture required for proper wound healing. Various concentrations of zinc and iron may be incorporated in solution to adjust or control release properties of the hydrogels. These components will be incorporated into a hydrogel during synthesis via an aqueous solution. A wound healing solution may comprise, for example, 5 to 30 mg/L of zinc, 5 to 50 mg/L of iron (in the form zinc chloride and iron sulfate, for example), approximately 100 mg/L sulphuric acid, and water. An acetate buffer with a low pH may also be incorporated into the hydrogel. The acidity of the solution keeps the pH below 3.0, which has also been shown to improve the recovery time of wounds. The low pH also may allow the hydrogels to change formation, releasing the healing agents.

Silver may also be incorporated in embodiments of the wound healing hydrogels described herein. Silver ions, which have antibacterial properties, may be added in conjunction with zinc and/or iron or separately. The concentration of silver may be in concentrations from 5 to 50 mg/L for the wound healing solution. One embodiment of the hydrogels for wound healing described herein comprise a Zinc: Iron solution comprising zinc cations at 0.030 mgs/ml and iron cations at 0.0195 mgs/ml in sulfuric acid solution of pH 3.0.

Alternatively, a fluorescent or luminescent marker can be conjugated to the particles, or encapsulated by the particles, for diagnostic purposes (e.g., for detecting binding of nanoparticles to target cells or tissues), or for studying trafficking of the particles in vivo, for example. Examples include luciferin/luciferase biomarkers or GFP, as well as fluorescent dyes (e.g., AMCA), many of which are well known. Further, these markers can be encapsulated within the nanoparticles to study the kinetics and environments of biomarker release.

The hydrogels may comprise further additives. Some agents of therapeutic benefit include, but are not limited to, any type of antibiotic, gallium salts (gallium salts have been shown to kill *Pseudomonas Aeruginosa* and disrupt biofilm formation in wounds and particularly burn wounds), silver ions which are known to be bacteriostatic, metal chelators such as EDTA, transferrin, lactoferrin, siderophores, and/or other proteins such as proteins that bind iron may be bactericidal because bacteria require free iron for growth, chlorohexidine or any other type of antiseptic compound, cell wall hydrolytic enzymes, such as the phage-derived lysins or lysostaphin, or other enzymes capable of being bacteriolytic for select Gram-positive organisms, proteins such as dispersin B or glucuronidase which are capable of disrupting biofilm formation, bacteriocins or other proteins that perforate the outer membrane of Gram-negative organisms, bactericidal peptides, such as defensins, histatins, protegrins, tachyplesins, and thionins, quorum sensing inhibitors that disrupt bacterial signals when to change growth patterns or respond to external stress, fibrinogen, thrombin, and Factor 13 for formation of blood clots which are particularly useful for field dressings of battlefield wounds, growth factors, cytokines, or chemokines (C5a or interleukin-8) that are chemo-attractant for neutrophils and other immune cells.

In some aspects, the invention provides a method for treating or preventing a bacterial infection, comprising, administering the nanogel described herein to a patient in need thereof. In particular, the invention finds use in treating wounds, including deep cavity wounds, hospital acquired infection, battlefield wound, and burns. In some embodiments, the patient has an antibiotic resistant bacterial infection. In some embodiments, the hydrogel is administered topically to the wound or infected region, or alternatively, is administered systemically, such as for patients showing signs or symptoms of sepsis or bacteremia, or at significant risk thereof.

Complications due to wound infection are the primary cause of morbidity among patients that suffer combat and non-combat related trauma, and are a leading cause of mortality in patients who survive the first few days after injury. The effects of these multidrug-resistant bacteria are even more devastating for burn patients or those who are otherwise immune-compromised.

In various embodiments, the nanogel compositions are administered to treat or prevent sepsis, cellulitis and skin abscesses, pneumonia, toxic shock syndrome, or endocarditis.

The present invention provides compositions to treat or prevent infection by a variety of bacterial pathogens, including drug-resistant pathogens. Examples of drug-resistant bacteria include: methicillin-resistant *Staphylococcus aureus* (MRSA), vancomycin-resistant *S. aureus* (VRSA), vancomycin-resistant *Enterococcus* (VRE), and multidrug-resistant *A. baumannii* (MRAB).

Non-limiting examples of disorders/diseases caused by bacterial infections, which may be treated or prevented in accordance with this disclosure, include, but are not limited to: pneumonia, bacterial meningitis, cholera, diphtheria, tuberculosis, brucellosis, campylobacteriosis, typhus, ear infections, including recurrent ear infections, gonorrhea, listeriosis, lyme disease, rheumatic fever, pertussis (Whooping Cough), plague, *salmonellosis*, scarlet fever, shigellosis, sinusitis, including chronic sinusitis, syphilis, trachoma, tularemia, typhoid fever, and urinary tract infections, including chronic urinary tract infections. For example, in some embodiments the chronic infection is infective endocarditis, which may be caused by *enterococcus*.

In some embodiments, the infection being treated or prevented is, for example, bacteremia, bacterial endocarditis, infections associated with external burns, infections associated with cystic fibrosis, prosthetic valve infections, native valve infection, infection associated with endometritis, infection associated with febrile neutropenia, infection associated with an in-dwelling medical device, intraabdominal infection, meningitis, infection associated with osteomyelitis, infection associated with pelvic inflammatory disease, infection associated with peritonitis, infections associated with pneumonia, infection associated with pyelonephritis, infection associated with skin or soft tissue, and infection associated with surgery.

Examples of infectious bacteria that may be involved or associated with an infection to be treated, include, but are not limited to: *Helicobacter pylorus, Borelia burgdorferi, Legionella pneumophilia, Mycobacteria* sp. (such as *M. tuberculosis*), *Staphylococcus aureus, Staphylococcus epidermidis, Neisseria gonorrhoeae, Neisseria meningitidis, Listeria monocytogenes, Streptococcus* sp., *Campylobacter* sp., *Enterococcus* sp., *Haemophilus influenzae, Bacillus anthracis, Bacillus cereus, Bifidobacterium bifidum. Corynebacterium* sp., *Clostridium* sp. (*perfringens, tetani, difficile*), *Enterobacter* sp. (e.g., *aerogenes*), *Klebsiella* sp. (e.g., *pneumoniae*), *Pasteurella multocida, Bacteroides* sp., *Fusobacterium nucleatum, Streptobacillus moniliformis, Treponema pallidium, Treponema pertenue, Actinomyces* sp, *Moraxella catarrhalis, Acinetobacter* sp. (e.g., *baumannii*), *Bordetella pertussis; Brucella* spp., *Francisella tularensis; Haemophilus ducreyi; Citrobacter* sp., *Escherichia coli; Proteus* sp., *Salmonella* sp. (e.g., *enteriditis, typhi*), *Shigella* sp., *Serratia marcescens, Yersinia* sp. (e.g., *enterocolitica, pestis*), *Aeromonas* sp., *Plesiomonas shigelloides; Vibrio* sp. (e.g., *cholerae, parahaemolyticus, vulnificus*), *Flavobacterium* sp., *Burkholderia* spp., *Chlamydia trachomatis, Chlamydophila pneumoniae, Chlamydophila psittaci, Coxiella burnetii, Ehrlichia chaffeensis, Legionella* spp., *Leptospira* spp., *Rickettsia rickettsii*, and *Treponema pallidum*.

Routes of administration include topical administration, intravenous administration, or by intramuscular, intraperitoneal, subcutaneous, intra-articular, intrasynovial, intrathecal, oral, or inhalation routes. In other embodiments, compositions are administered to infected eyes, ears, or sinus.

Other ligands can be incorporated into the hydrogel composition, other than antibiotics, to impart other targeting properties, such as targeting of mammalian tissues and cells, including cancer cells. For example, the nanoparticles may be functionalized with groups that are capable of binding with a receptor on a cell (e.g., a cancer cell) chemically attached to the nanogel or nanoparticle. In a specific embodiment, the hydrogel comprises polymeric segments derived from polysaccharide (e.g., dextran) and polymeric segments derived from poloxamers that are cross-linked, and a targeting agent chemically attached to the polymeric network. The soft cell properties of dextran and the stabilizing, thermally responsive properties of poloxamers and poly(epoxides) offer a safe, non-toxic, and controlled drug delivery vehicle. Polysaccharide-poloxamer hydrogels, nanogels, and nanoparticles are biodegradable, bioabsorbable and will deteriorate to elements naturally excreted or absorbed by the body allowing release of medicaments at the targeted site.

Targeting agents of the nanogels or nanoparticles are capable of binding to a receptor in the body. As used herein, a receptor is a molecule or a portion of a molecule found on the surface of a cell that receives chemical signals from substances outside the cell. Binding to the receptor may be through covalent bonding, ionic bonding, complexation, hydrogen bonding, dipole-dipole interaction, van der Waals forces or any combination of such associations between at least one site of the targeting agent and at least one site of the receptor, as long as the binding is sufficiently strong to essentially form a target-receptor associate. The targeting agent may be a monoclonal antibody or fragment, for example, or a soluble factor or natural ligand for the targeted receptor.

In additional embodiments, the nanoparticle drug delivery system comprises medicaments, either conjugated or encapsulated by the nanoparticle. The targeting agent attaches the nanoparticle to the target receptor and the medicaments may be released from the nanogel or nanoparticle as the poloxamer based segment is thermally or otherwise degraded and the dextran based segment is enzymatically degraded. This provides a drug delivery system with targeted medicament delivery. The medicaments may be for therapeutic treatment of a wide variety of diseases and ailments that would benefit from such targeted delivery. For example, the medicament may be at least one of a pharmaceutical, chemotherapeutic agent, enzyme, hormone, cytokine, polynucleotide, nicotinic acid, glucocorticoid, budesonide, mitomycin C, monoclonal antibody therapeutic, anti-inflammatory agent, naproxen, aspirin, ketoprofen, ibuprofen, diclofenac, indomethacin, a prodrug, a fluorescent labeling agent or radiolabelled biomarker. The nanoparticle targeting nanogel or nanoparticle may have an average diameter in the range of 1 nanometer to 1000 nanometers or the nanogel targeting molecule may have an average diameter in a range from 20 nanometers to 250 nanometers, for example. An optimal size of hydrogel nanoparticles for prolonged in vivo blood residence is in the 20-200 nm range.

In some embodiments, enzymes may be medicaments chemically attached or encapsulated into the polysaccharide-poly(epoxide), polysaccharide-poloxamer or dextran-pluronic F-127 hydrogel and/or nanoparticles. The enzymes may be conjugated to dextran or poloxamers monomers prior to polymerization or attached to the surface of the nanogel or nanoparticle. Enzymes that may be chemically attached to or encapsulated within the hydrogel include, but are not limited to, α-amylase, arginase, asparaginase, carboxypeptidase, catalase, β-galactosidase, hyaluronidase, NAD+, streptokinase, papain, α-chymotrypsin and trypsin.

In other embodiments, dextran may be functionalized to attach prodrugs by preparing carboxymethyl dextran, dextran sulphate, or diethylaminoethyl dextran. Diethylaminoethyl dextran is an example of a charged dextran derivative that may form complexes with various chemical entities including, for example, bleomycin, isometamidium and gentamicin may form a dextran sulphate complexes and proteins and nucleic acids that may be chemically attached to the hydrogel or nanoparticle. Hormones that also may be linked to, or encapsulated by, the hydrogel include, but are not limited to, oxytocin and vasopressin.

EXAMPLES

Example 1: Pluronic F-127 Diacrylate Synthesis

Pluronic F-127 (poloxamer) obtained from BASF is dissolved into a 10% solution with dichloromethane (DCM) in a 2-neck flask with a stir bar. Triethylamine (TEA) and acryloyl chloride are added to the flask in the molar proportion of 3 times excess to the [—OH] end groups of the poloxamer and the flask stirred at 80° C. for 3 hours under reflux. After such acrylation, the solution is filtered and precipitated in hexane to recover the poloxamer diacrylate and then dried to remove residual hexane. This reaction may also be performed with any soluble materials that possess alcohol groups, so other polymers may be modified accordingly.

Example 2: Dextran Acrylate Synthesis

Commercially obtained dextran is dissolved into a 10% solution with DMSO in a 2-neck flask with a stir bar. Triethylamine and acryloyl chloride are added to the flask in the molar proportion relevant to the number of [—OH] end groups which are desired to be acrylated (may be variable based upon the desired degree of cross-linking) and the flask is stirred at 80° C. for 3 hours to allow sufficient conversion. After such acrylation, the dextran acrylate DMSO solution is filtered and precipitated in isopropanol to purify the dextran-acrylate and subsequently dried. The grade and type of dextran may be chosen in order to control, the properties as well as the degree of modification.

Other methods of hydrogel formation can be used without monomer modification steps such as a radical polymerization process. Stable nanogels of desired size and shape may be produced with an inverse mini-emulsion polymerization process such as a controlled radical polymerization inverse mini-emulsion process.

The polysaccharide-poloxamer hydrogel may be conjugated with functional group targeting systems for site specific therapeutic drug delivery. More specifically, polysaccharide-poloxamer nanogels (nanogels are hydrogels which have an average diameter between 1 and 1000 nanometers) may be functionalized to be biocompatible, biodegradable, bioabsorbable and thermally responsive to body temperatures that will trigger a controlled release of medicaments.

Inverse emulsion polymerization may be used for fabrication via cross-linking, of acrylate derivatives of dextran and diacrylate derivatives of poloxamers. This polymerization technique allows for control over size, is versatile in respect to initiation and composition, and may proceed to full double-bond conversion in a relatively short time. Incorporation of functional polysaccharide co-monomers, like dextran, in the polymeric network affords the possibility of further conjugation, such as the addition of biomarkers, fluorescent labeling, and macromolecular prodrugs, for example. Moreover, hydrogel nanoparticles in the range of 50-250 nm may be designed to maintain a state of stability as aqueous dispersions, resist aggregation, and can be freeze-dried as solid powders for long-term storage without degradation.

Example 3: Dextran Modification for Further Reaction

Figure 2:
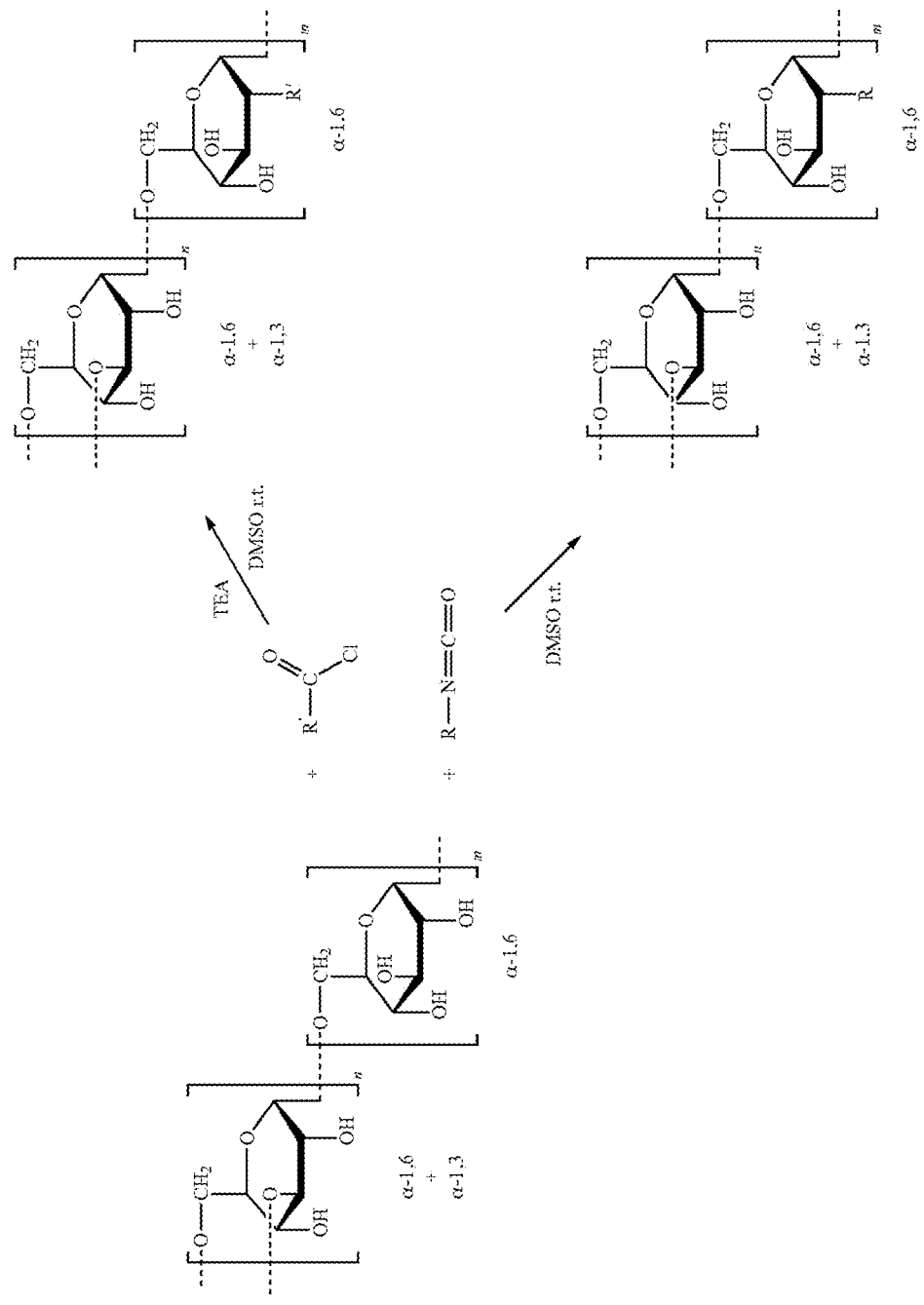
FIG. 2 illustrates functionalization of dextran with acyl chloride or isocyanate.
Figure 3:
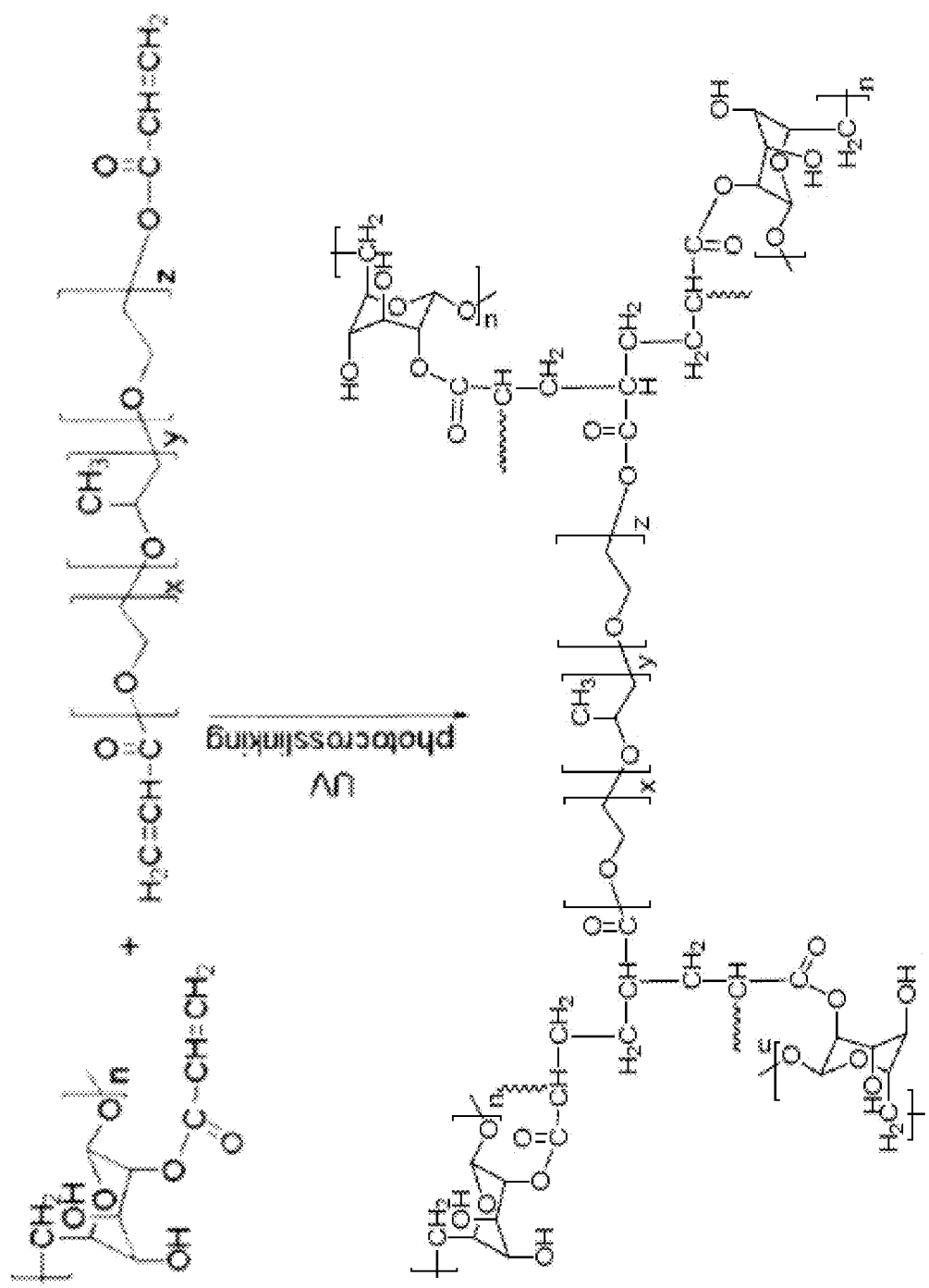
FIG. 3 illustrates crosslinking of functionalized dextran (dextran acrylate) and functionalized poloxamer (poloxamer diacrylate).

Dextran may be functionalized directly through reaction with the hydroxyl groups or indirectly by reaction with a linking functional group and subsequent further functionalization. The hydroxyl groups may easily react with a variety of linking functional groups including, but not limited to, isocyanates and, acyl chlorides. A generalized reaction for functionalizing dextran is shown in FIG. 2. In this case "R" and "R1" are generally any group that has some desirable property to be applied for this process.

Example 4: Copolymerization with Dimethylaminoethyl Methacrylate (DMEAMA) and SiRNA The poloxamer diacrylate (Example 1) and dextran acrylate (Example 2) monomers are co-dissolved with DMEAMA and/or siRNA in an aqueous solution at various concentrations prior to polymerization. Additionally Irgacure 2959 may be dissolved into this formulation at about 1-5% w/w monomers to make the resultant hydrogel photoactive.

Additional monomers may be substituted for or added in addition to the DMEAMA to provide additional properties to the resultant hydrogel, including, but not limited to, hydrogen bonding monomers (n-vinyl pyrrolidinone, acrylic acid), thermally sensitive monomers (N-isopropyl acrylamide), or additional cross-linking agents (polyethylene glycol diacrylate) so as to add or modify properties of the resultant particles. Examples of potential monomers are shown in FIG. 4.

Example 5: Exemplary Dextran Conjugation Chemical Processes

Direct Esterification

The dextran ester prodrugs of several drugs like nicotinic acid, naproxen, aspirin, ketoprofen, ibuprofen, diclofenac and indomethacin have been synthesized with the aim of achieving prolonged release properties. Dextran, can be attached to the drug to form a prodrug by a direct linkage, attachment through linker group. In direct linkage model, drug is directly linked to the hydrogel, which would release the active agent in a predictable manner by thermal degradation, pH dependent hydrolysis, or other degradation of portions of the hydrogel.

Dextran can be attached to the drug to form a prodrug by a direct linkage, attachment through linker group or through covalent bonding, ionic bonding, complexation, hydrogen bonding, dipole-dipole interaction, van der Was forces or any combination of such associations. In direct linkage model, drug is directly linked to the hydrogel, which would release the active agent in a predictable manner by thermal degradation, pH dependent hydrolysis, or other degradation of portions of the hydrogel.

Carbonate Ester Method

Drugs containing a hydroxyl group can be coupled to dextran in the form of carbonate ester linkages either by activating the carrier hydroxyl group by phosgene followed by addition of alcoholic drug or by preparing chlorocarbonate dextran esters of the drug which are further used as intermediates in the construction of enzyme conjugates.

Periodate Oxidation Method

Dialdehyde dextran is obtained by periodate oxidation of dextran, which is condensed with amino compounds yielding schiff bases. The subsequent reduction with sodium borohydride is performed in order to stabilize the conjugate.

Carbamate Ester Method

The carbamate ester liganded conjugates exhibit prolonged duration of activity and reduced toxicity in proportion to the free drug.

Bromide Activation Method

Cyanogen bromide activation of dextran is probably can be used reaction to achieve covalent attachment of compounds possessing an amino function to dextran.

Acid Cleavable Linking Groups

Conjugates may be added to polysaccharides by acid cleavable functional groups to add prodrugs to the nanogel or nanoparticles.

Targeted Conjugations of Dextran

The chemical composition of polysaccharide-poloxamer hydrogels provides for chemical modifications for attaching targeting agents for receptors and attaching or encapsulating medicaments for therapeutic treatment of a wide variety of diseases and ailments. Dual conjugations may also be prepared, for example, a polysaccharide-poloxamer nanoparticle may comprise both a cancer cell luminescent biomarker conjugate and a cancer cell targeting prodrug conjugate for real time theranostics.

Additionally, polymyxin B (PMB) may be conjugated to a polysaccharide-poloxamer nanoparticle. Polymyxin B is an antibiotic used against gram-negative bacterial infections. Polymyxin B is a targeting agent that binds to receptors on cell membranes of Gram Negative bacteria resulting in a change in its structure, making the cell wall more permeable.

Example 7: Dextran-Polymyxin Conjugate Synthesis

The polysaccharide-poloxamer nanoparticle may be formed by conjugating the polymyxin B (PMB) to the monomers prior to the polymerization or by conjugating the PMB to the surface of the polysaccharide-poloxamer nanoparticle. For example, dextran acrylate (Example 2) may be dissolved in 20 ml water, cooled to 0° C., and 5-300 mg of 1-cyano-4-dimethylamino pyridinium tetrafluoroborate (CDAP) is added and mixed for 30 seconds. TEA (0.2 M, 0.04 ml per 5 mg CDAP) is added dropwise with vigorous stirring, and the entire reaction mixture is transferred to 80 ml of ice cold ethanol containing 1 ml of 10 N HCl. The dextran precipitates, and the precipitate is removed by cold centrifugation at 1000 g, for 5 min, and solubilized in 20-50 ml of 0.25 M Na-bicarbonate buffer at pH 9.0. To this mixture 600-1000 mg of PMB (either powdered or solubilized in water) is added and stirred for 24 hours at 8° C. The entire reaction mixture is then transferred to 50,000 molecular weight cut-off dialysis tubing and dialyzed against 0.05 M pyrogen-free phosphate buffer for 6-10 days.

Example 8: Alternate Dextran-Polymyxin Conjugate Synthesis

Dextran acrylate (Example 2) may be dissolved in water and reacted with sodium periodate in order to generate functional aldehyde groups available for subsequent reaction. The thus activated dextran will then be dissolved in DMSO along with polymyxin-B and reacted to conjugate using a commercially available hetero-bifunctional photoaffinity cross-linker such as p-azidobenzoyl-hydrazide (ABH, Pierce). This solution is handled in the dark and allowed controlled periods of exposure to UV light via Blak-Ray B100A. Polymyxin-B in double-distilled water (0.5) is combined with the hetero-bifunctional covalent ion crosslinking reagent azidohenzoyl hydrazide, 50 µL of 50 mM in DSMO. Following constant stirring in a 37° C. water bath for 60 min, the preparation is exposed to light-flashes (5×3 sec) from a halogen lamp source. Preparation of Hydrogel involves limited oxidation under dark conditions with sodium periodate (NalO$_4$ 30 mM, pH 7.0, 1.0 mL). During the final phase (II) of the semisynthesis procedure, the polymyxin-azidohenzoyl hydrazide reactive intermediate complex is combined with partially oxidized Hydrogel fractions and the resulting reaction mixture is stirred continuously at 24° C. for 30 minutes.

Example 9: Short Interfering Ribonucleic Acids (siRNAs)

siRNAs can be designed to target several debilitating diseases. Inhibiting, a target protein using siRNA's can effectively down regulate either the function of an individual gene or group of genes without eliciting a toxic or an immune response. Post-transcriptional gene silencing occurs through RNA interference, where the double stranded RNAs (dsRNAs) are cleaved into 21-23 nucleotide fragments (i.e., short interfering RNA:siRNA). Cleavage occurs by a cellular endonuclease of the ribonuclease-III type called DICER. The short duplexed siRNA's are unwound by a helicase with the antisense strand becoming incorporated into the multi-component RNA-induced silencing complex (RISC). This moiety mediates sequence-specific gene silencing by cleaving the target mRNA.

A siRNA phosphodiester backbone is anionically charged and naked siRNA does not pass through the cell membrane. The electrostatic repulsion between naked siRNA and the anionic cell membrane surface prevents naked siRNA endocytosis. Therefore, a delivery system is required for efficient transport and release. The most commonly used gene delivery systems can be divided into biological (viral) and non-biological (non-viral) systems. Each group has its own advantages and limitations. Biological carriers and viruses possess high efficiency in siRNA transfer but are difficult to produce and may be toxic. These limitations favor non-biological systems for siRNA delivery.

Non-viral delivery systems include peptides, lipids (liposomes), dendrimers and polymers with cationic charges that interact with the negatively charged siRNA through electrostatic interactions. A recent review focused on use of precise polymer conjugates as nucleic acid delivery and concluded that the materials for delivery of siRNA had to be precise polymers, with defined site-specific conjugation strategies that provided multifunctional conjugates for nucleic acid transport. Dendrimers, defined peptide carriers, sequence-defined polyamidoamines assembled by solid-phase supported synthesis, and precise lipopeptides or lipopolymers have been characterized for pDNA and siRNA delivery. Conjugation techniques such as click chemistries and peptide ligation are available for conjugating polymers with functional transport elements such as targeting or shielding domains and for direct covalent modification of therapeutic nucleic acids in a site-specific mode. However, the efficacy of RNAi in vivo depends upon efficient delivery of the intermediates of RNAi, such as short interfering RNA (siRNA).

Example 10: Additional Gram Negative Targeting Prodrug Conjugations for Dextran Co-Monomer of Polysaccharide-Poloxamer to Deliver Antibiotics Penicillin, Carbapenem, Cephalosporin, and Glycopeptide antibiotics (e.g., vancomycin) inhibit bacterial cell wall biosynthesis and afford an opportunity as potential conjugates of the polysaccharide-poloxamer drug delivery system to target gram positive bacteria (including multiple drug resistant bacteria). Other antibiotics often act in the cell and to be effective these antibiotics must penetrate the cell wall. Aminoglycosides, for example, have to be actively transported across the bacterial cell membrane. Glycoproteins, for example, vancomycin and teicoplanin, are unable to penetrate the outer membrane of gram-negative organisms and thus have restricted activity against these organisms.

Example 11: Amine Conjugation on Polysaccharide-Poloxamer Hydrogel for Cationic Charged Nanogel Delivery Amines may also be conjugated to the polysaccharide-poloxamer nanoparticles or hydrogel. Cationically charged compounds may then be chemically attached to the nanoparticles or hydrogel. Nanoparticles with a primary amine at the surface promote higher rates of phagocytic uptake. To produce a charged Polysaccharide-poloxamer nanoparticle, an amine can be conjugated to dextran prior to polymerization or the surface of the nanoparticle may be functionalized after polymerization.

To incorporate amine group into dextran-acrylate (Example 2), dextran-acrylate may be further reacted with 3-chloropropylamine hydrochloride in the presence of triethylamine. An example of dextran-acrylate-propylamine synthesis is as follows.

Pre-dried dextran-acrylate (2.0 g) is dissolved in anhydrous DMSO under nitrogen gas at room temperature. Triethylamine (11.2 ml) is then injected into the above solution. Meanwhile, 3-chloropropylamine hydrochloride (4.8 g) is dissolved in DMSO and then added to the above solution drop wise, and stirred for 5 hours at 50° C. Dextran-acrylate-propylamine is obtained by precipitating the filtered solution into excess cold isopropyl alcohol. The product is further purified three times by dissolution/precipitation with DMSO/cold isopropyl alcohol. The final product is dried overnight at room temperature under vacuum before further use.

"Charged"-siRNAs or other charged medicaments or targeting agents may then be chemically attached to or encapsulated in the amine functionalized polysaccharide-poloxamer nanoparticle produced from the amine functionalized dextran-acrylate and delivered as targeted cargo to bacteria.

Example 12: Antibody Conjugated Polysaccharide-Poloxamer Nanoparticles for Treatment of Triple Negative Breast Cancer Triple negative breast cancer (TNBC) is an aggressive breast cancer phenotype characterized by lack of expression of estrogen receptor (ER) and progesterone receptor (PR), as well as the absence of overexpressed human epidermal growth factor receptor-2 (HER-2). As noted below, this threatening disease is far reaching in its effects. About 15% of breast cancer patients are diagnosed with triple negative breast cancer.

TNBC is generally accepted as a clinical surrogate for basal-like breast cancer. All basal-like breast cancers are not triple negative however. This phenotype is associated with an early age of cancer onset, high chance of presentation with metastases and high proliferative index. The prognosis of patients with this type of tumor is very poor because of non-responsiveness to hormonal therapy or poor response to the therapy of choice in breast cancer (e.g., Tamoxifen). Hence, there is an urgent and unmet need for efficacious therapeutics to treat TNBC. Anti-EGFR therapy has been increasingly recognized as an important treatment for TNBC patients and is being evaluated in advanced clinical trials for patients with metastatic TNBC. High expression of epidermal growth factor receptor (EGFR) induces erroneous development and unrestricted proliferation in a number of human malignancies, including breast cancer and also prostate cancer. This receptor has long been considered as a potential target for the treatment of a number of cancer types. EGFR mRNA is detected more frequently and at higher levels in basal-like breast cancers. Antibody dependent cellular cytotoxicity is recognized as prominent cytotoxic mechanism for therapeutic monoclonal antibody. There are a number of monoclonal antibodies (mAbs) currently available on the market for cancer treatment and a plethora being evaluated in clinical trials exhibiting mixed therapeutic outcomes. For an optimum therapeutic response, monoclonal antibodies (mAbs) should exhibit a sufficiently long half-life to interact with the target tissue effectively, have the capability to get internalized in the tumor interior, have no inducement of an immune response, and deliver sufficient potency. Unfortunately, most of the marketed mAbs do not fulfill all of these requirements, thus providing a suboptimal therapeutic response.

Nanotechnology is an area of manipulation/construction of structures in a nanometer size range. The chemical/physical properties of the construct can radically change at this level, which can be exploited to deliver the antibody to uncharted destinations efficiently and also carry more antibodies precisely to the site of action which will elicit greater effect. An antibody capable of identifying tumor antigens can be anchored on the surface of the nanocarriers to increase the targeting efficiency, thereby increasing drug accumulation in the tumor tissue. These antibody conjugated nanocarriers can provide long circulation and significantly higher tumor accumulation properties (due to enhanced permeability retention effect) which yield significant improvements in therapeutic efficacy.

Some of the other examples of marketed antibody conjugates are with cytotoxic drugs (MYLORTAG) or radioisotopes (PROSTASCINT). However, to date, there are no commercial antibodies conjugated to nanoparticles available in the cancer treatment regimen. The available data suggests a significant edge for antibody conjugated nanoparticles in cancer therapy in terms of efficacy and a reduction in toxicity. The treatment of TNBC presents a momentous challenge to the oncologist often faced with limited therapeutic options coupled with aggressive and unresponsive tumors, Thus, development of an efficient therapeutic system for effective treatment, modality of TNBC is an urgent need. This could be addressed by conjugating clinically relevant antibody to nanoparticles.

A therapeutic modality for the treatment of TNBC in the form of EGFR antibody conjugated to polysaccharide-poly (epoxide) nanoparticles can be developed to yield significant therapeutic benefits over current therapies.

A revolutionary new biocompatible hydrogel drug delivery platform based on a polymeric network of cross-linked polysaccharide monomers and epoxide monomers will be used to form nanoparticles. In a particular embodiment, a hydrogel synthesized from crosslinking a modified dextran (a natural polymer) and another FDA approved polymer (PLURONIC F-127) also modified to facilitate (esterification) UV crosslinking will create the copolymer hydrogel. PLURONIC F-127 is biodegradable and also provides thermally responsive properties when incorporated into the nanoparticle. The elevated and narrow range of human body temperature offers an ideal trigger for thermal responsive hydrogels that employ the block copolymer PLURONIC F-127 and offers "tunable optimization" per application for "tailored" controlled therapy. This hydrogel is amenable for conversion to nanoparticles either by top down or bottom up approaches with narrow particle size distribution. A bottomup approach constructs nanoparticles from basic building blocks like atoms or molecules as in a miniemulsion polymerization process. A top-down approach produces nanoparticles from larger materials from physical processes such as, for example, grinding or milling or through chemical-based processes (bond breaking). Production of the hydrogels by inverse mini-emulsion polymerization and crosslinked in-situ by free radical mechanisms is advantageous in some embodiments, because this approach has a lesser energy demand and eliminates the need for high energy equipment.

EGFR antibody conjugated nanoparticles derived from polysaccharides and poloxamers would yield better therapeutic response in TNBC. For example, these mAb conjugated nanoparticles may exhibit higher accumulation at the tumor site due to an enhanced permeability effect; the hydrophilic surface of the nanoparticles may render them long circulating; and biocompatible cargo is not expected to yield any toxicity or immune reactions.

These properties of the polysaccharide-poly(epoxide) nanoparticles may result in better treatment of TNBC. Commercially available or clinically evaluated EGFR mAb would be preferred, as it would propel the development cycle significantly and shorten the time for market entry. The EGFR mAb may be selected from, but not limited to, Cetuximab, Panitumumab, or Zalutumumab. The nanotechnology will yield viable options to otherwise non responsive and aggressive TNBC. Hence, embodiments of the polysaccharide-poly(epoxide) will yield a therapeutically efficient, commercially viable niche formulation to treat TNBC with a scope of extending the indications to other cancer types exhibiting EGFR overexpression such as prostate cancer.

Example 13: Formulation of Polysaccharide-Poloxamer Nanoparticles

In this embodiment, a "bottom up" technique for formation of nanoparticles using inverse emulsion polymerization will be used to produce the polysaccharide-poloxamer nanoparticles. This technique has been developed and optimized. The inverse emulsion polymerization technique selected for the production of nanoparticles is simple, versatile and easy to scale-up. The size of the macromonomer inverse emulsion droplets can be manipulated by varying emulsifier concentration. In this embodiment, polysaccharide-poloxamer nanogels of desired size may be produced with the controlled droplets of water soluble dextran-acrylates UV cross-linked to PLURONIC F-127 diacrylates in solution. Photopolymerization proceeds very fast but irradiation may be allowed to proceed for an extended time, such as for 1 hour to ensure substantially complete polymerization.

Other polysaccharides can be cross-linked to PLURONIC F-127 or other poloxamers (or more generally poly(epoxides), in inverse emulsion photopolymerization, provided they are soluble in water and that the monomers contain, or are functionalized with, polymerizable groups.

Dextran-pluronic F-127 nanoparticles, other polysaccharide-poloxamer, or polysaccharide-poly(epoxide) based hydrogels can be obtained via inverse emulsion photopolymerization. Nanoparticle size can be controlled through choice of emulsifer(s), monomer and emulsifier concentration, and polymerization process conditions.

Example 14: Conjugation of EGFR Antibody to Dextran-Pluronic F-127 Nanoparticles, Other Polysaccharide-Poloxamer, or Polysaccharide-Poly(Epoxide) Nanoparticles In this embodiment, EGFR antibody will be conjugated to the surface of dextran-pluronic F-127 nanoparticles after formation of the nanoparticles. Alternatively, the EGFR antibody may be conjugated to the monomers with subsequent formation of nanoparticles. A mAb within the nanoparticle matrix would elicit therapeutic response after degradation of the nanoparticle. The surface pendent mAb recognizes the target receptor and attaches to them to elicit bioactivity of the cell.

The Fe-directed conjugation of the antibody molecules can be made through reductive amination coupling between the free amino groups in the Fe-region of the antibody and reactive aldehyde groups. To create reactive aldehyde groups on the nanoparticles surface, oxidation of dextran may be carried out under mild conditions using sodium iodate and a fixed concentration of dextran-pluronic F-127 nanoparticles. This reaction is performed in the dark and under an inert atmosphere. The oxidation reaction is quenched by the addition of ethylene glycol. The nanoparticles will be purified by dialysis. To this, different concentrations of EGFR antibody are added and incubated. This conjugated structure is stabilized by reduction using sodium borohydride. Finally, the nanoparticles are purified and concentrated using spin filter. Optionally, fluorescent tagged mAB will also be used as marker for cellular uptake and trafficking study.

The size and zeta potential of dextran-pluronic F-127 nanoparticles can be evaluated by dynamic light scattering technique. This technique will also be used to determine any changes in the nanoparticles' characteristics due to mAb conjugation. The shape of nanoparticles can be accessed by transmission electron microscopy after negative staining with uranyl acetate or phosphotungstic acid or osmium tetroxide. Surface characteristics of mAb conjugated dextran-pluronic F-127 nanoparticles can be tested to evaluate the effect of the conjugation process.

Example 15: In Vitro Cell Culture Studies and In Vivo Studies

A number of different cell lines can be used to evaluate the developed mAb conjugated dextran-pluronic F-127 nanoparticles, including human breast cancer cell lines MDA-MB-468 (TNBC, EGFR-positive), SKBR-3 (EGFR-positive), BT-474 (EGFR-positive), and MCF-7 (EGFR-negative). The dextran-pluronic F-127 nanoparticles conjugated with different mAb concentrations, naked mAb, and unconjugated dextran-pluronic F-127 nanoparticles will be evaluated in different cell culture studies such as proliferation assay, cell cycle assay, and western blot analysis and the cell uptake will be evaluated by (fluorescent conjugated mAb) flow cytometry, confocal microscopy, etc.

These studies will be designed to check retention of bioactivity of mAb after the conjugation process, and optimization of mAb concentration on the dextran-pluronic F-127 nanoparticles to yield optimal bioactivity. In vitro and in vivo evaluation of three prototype EGFR monoclonal antibody conjugated dextran-pluronic F-127 nanoparticles will be performed. The primary objective of these studies is to determine anti-tumor activity of these agents with a model of breast cancer that is EGFR positive and is ER neg., PR neg. and HER2 neg. This model we determine whether the antibody targeting EGFR conjugated to dextran-pluronic F-127 has superior efficacy compared to the unconjugated antibody.

Prior to in vivo efficacy testing of the nanoparticles it will be important to determine their safety upon intravenous delivery to immunocompromised athymic nude mice. Also, prior to evaluating in vivo tolerability of the antibody conjugated nanoparticles, toxicity will be tested in vitro, for example, with the MTT assay using the MDA-MB-468 breast cancer cells. Hemolysis and micronucleus test of genotoxicity can be performed.

Evaluation of toxicity of dextran-pluronic F-127 nanoparticles is an important step in development of any nanotechnology based therapeutic agent. In vitro model systems provide a rapid and effective means to assess nanoparticles for specific toxicological endpoints. These studies allow for elucidation of the mechanism of interaction of nanoparticles with cells. Hence in vitro studies can be effectively used to establish specific toxicological profiles of developed nanoparticles and would help to design the protocol of in vivo studies.

The MTT assay can be used determine the effect of prototype antibody conjugated nanoparticles on MDA-MB-468 cell viability and metabolic activity measured by the reduction of the tetrazolium salt MTT to insoluble MTT-formazan. The unconjugated dextran-poloxamer nanoparticles will also be tested as control. Moreover the hemolysis and micronucleus genotoxic test will measure different cytotoxicity endpoints of the antibody conjugated dextran-poloxamer nanoparticles.

The results from these studies will instruct the optimal concentration of the antibody formulation that will be tested in the in vivo efficacy and compared with the naked antibody, control unconjugated nanoparticles and saline.

For athymic nude mice study, mice receive treatment intravenously twice a week, and are carefully observed every day for at least two weeks for any sign of distress, abnormal behavior, body weight loss, morbidity, and mortality. Gross examination of organs is performed. The results from this study will be useful to assess safety of antibody conjugated nanoparticles in mice prior to testing their efficacy.

The MDA-MB-468 tumor cells are implanted in mice for this study, and are first transfected with luciferase lentiviral particles and implanted into the mammary fat pad of five mice to ensure the tumors grown in, vivo retain bioluminescence. Then the luciferase-labeled tumor cells will be harvested from in vitro cultures and implanted with 50% matrigel in the mammary fat pads of nude mice (left side, $5\times10^6$ per mouse). When the tumors reach an average size of at least 130 mm$^3$ the mice will be randomized and distributed into 5 groups of 10 mice/each group with similar tumor size and bioluminescent signal measured by the Lumina Instrumentation after intraperitoneal injection of D-luciferin (15 mg/ml, 200 µl). The five treatment groups are two prototype mAB conjugated polysaccharide-poly(epoxide), polysaccharide-poloxamer, or dextran-pluronic F-127 nanoparticles formulations, the unconjugated monoclonal antibody, the unconjugated nanoparticles, and saline. Treatment is delivered intravenously twice a week for 4 weeks. The tumors are calipered one a week or more often, and imaged with the Lumina Instrument once a week; at the end of the study, the mice are euthanized three days after last treatment and the tumors harvested and fixed in 10% formalin for histology and analysis of tissue morphology.

Example 16: Mannosylation of Dextran-Pluronic F-127 Hydrogel

Tuberculosis (TB) is the leading cause of death in the world from a bacterial infectious disease. The disease affects 1.8 billion people yearly, equal to one-third of the entire world population.

The treatment of tuberculosis requires long-term antibiotic therapy. Because administration of a single drug often leads to the development of a bacterial population resistant to that drug, effective regimens for the treatment of TB must contain multiple drugs to which the organisms are susceptible. Active tuberculosis, particularly if it's a drug-resistant strain, will require several drugs at once. The most common medications used to treat tuberculosis include Isoniazid, Rifampin (Rifadin, Rimactane), Ethambutol (Myambutol), and Pyrazinamide.

*Mycobacterium tuberculosis* (MTB) is the etiologic agent of tuberculosis in humans. Humans are the only reservoir for the bacterium. Targeted antibiotic therapy improves the efficacy of treatment by concentrating the drugs close to *mycobacterium*. Once attached to a macrophage, the causative agent of tuberculosis, MTB avoids cellular defenses and uses the cell to replicate. The high concentration of lipids in the cell wall of *Mycobacterium tuberculosis* has been associated with impermeability to stains and dyes, resistance to many antibiotics, resistance to lethal oxidations and survival inside of macrophages. Polysaccharide-poloxamer targeting of MTB is accomplished by using mannose as a homing device.

Mannosylation of the dextran monomer enables the multidrug releasing delivery system, Polysaccharide-poloxamer, to target the macrophage. The *Mycobacterium tuberculosis* phagosome interacts with early endosomes and is accessible to exogenously administered transferrin.

The development of a polysaccharide-poloxamer delivery vehicle is based on dextran linked to mannose, to target the macrophage, for multidrug therapeutic release into the phagosomal vacuole. Water-soluble polysaccharide-poloxamer hydrogel can accommodate mannose homing residues (endocytosis by the target cell via a specific receptor) thus increasing the affinity for the target. Targeting is accomplished through ligand recognition by human mannose receptors.

To synthesize MTB targeted nanogels and/or nanoparticles, the monomers such as, but not limited to, the dextran monomer of the polysaccharide-poloxamer drug delivery carrier may be conjugated to mannose which acts as a targeting agent to direct multiple antibacterial releasing Polysaccharide-poloxamer into macrophages.

Dextran is purified to get fractions with weight-average molar masses of 64,000, 90,000, or 95,000 g/mol and with a weight-average molar mass/number-average molar mass ratio of 1.2.

Norfloxacin can be linked to mannosylated dextran using a peptide spacer arm. This conjugate shows more efficacy against *mycobacterium* than plain norfloxacin.

Example 17: Methods of Producing a Polysaccharide-Poloxamer Nanoparticle

The polysaccharide and poloxamer may be cross-linked with any polymerization process or appropriate cross-linking reaction including radical polymerizations, emulsion polymerizations, inverse miniemulsion polymerization, controlled polymerization, LTV initiated cross-linking, e-beam curing, ionic gelation polymerization or other polymerization process. The process, component concentrations and the process parameters may have a significant effect on the properties of the hydrogel or nanoparticles such as, but not limited to, rates of diffusion of pharmaceuticals out of the hydrogel membrane as well as in vivo half-life.

The ratio of polysaccharide to poly(epoxide), the molecular weight of the polysaccharide and/or the poly(epoxide), the chemical composition of the polysaccharide and/or the poly(epoxide), the relative lengths of the ABA block of the poloxamer, the degree of self-organization prior to cross-linking, the cross-linking functionality, as well as other factors may affect the physical and chemical properties of the hydrogel. For example, the mechanical strength of the hydrogel or polymeric network can be adjusted by more or less polysaccharide (in some embodiments, dextran) which will produce a different hydrogel or polymeric network with different mechanical strength and a different time controlled delivery of a drug for drug delivery applications. The chemical composition and size are important factors, which are indicative of the capability of the particles to penetrate into biological cells.

An inverse miniemulsion polymerization process for the production of nanoparticles is preferred because it is simple, versatile and easy to scale-up. A number of different monomers may be included in the cross-linked, hydrogel network of the nanoparticles, providing a flexible way of regulating material properties and introducing functionality, incorporating electrostatically charged and reactive functional groups by copolymerization of appropriate monomers. Inverse emulsion photopolymerization is a controllable method for preparing "more defined" nanoparticles. The aqueous macromonomer nano-droplets are "stabilized" by a cross-linking polymerization of acrylic derivatives, which preserves the structure of the nanoparticles. The nanoparticles produced present a capacity (nanodomain) of incorporating hydrophobic drugs.

In one embodiment, the aqueous phase, containing eosin Y (sensitizer), triethanolamine (initiator) and Pluronic F-127 diacrylate mixed with dextran diacrylate, is dispersed in hexane by sonication with the utilization of the powerful surfactant, Span 65, in the oil-to-water protocol. After photopolymerization, nanoparticles can be by removed from the hydrophobic emulsifier through repeated n-hexane washing.

The surfactant, Span65, is dissolved in hexane by sonication. Nonionic surfactants such as Span and/or Tween may be used in the reaction media. An aqueous solution of dextran acrylate, Pluronic F-127 diacrylate, triethanolamine, and eosin Y is added to the oil phase (oil-to-water weight ratio=65/35) and an inverse emulsion can be formed. The inverse emulsion can be illuminated with an Ar ion laser for 1 hour, at room temperature, under magnetic stirring (400 rpm). After illumination, the inverse emulsion can be poured into centrifuge tubes containing n-hexane and water. The aqueous phase is extracted with n-hexane to remove the surfactant and then dialyzed against water to remove the initiator and non-reacted macromonomers.

Again, conjugation of targeting agent(s) onto the alcohol reactive groups of the modified dextran (polysaccharide) co-monomer may be a first step in the production process of targeting therapeutic nanoparticles.

Inverse emulsion polymerization process has the ability to "control nanoparticle size" distribution. The size of the macromonomer inverse emulsion droplets decreased with increasing emulsifier concentration. Polysaccharide-poloxamer nanogels of desired size are produced with the controlled droplets of water soluble dextran acrylates UV cross-linked to Plutonic F-127 diacrylates in solution. Photopolymerization proceeds very fast but irradiation may be carried out for an extended period to ensure the desired degree of polymerization. Other polysaccharides can be cross-linked to Pluronic F-127 in inverse emulsion photopolymerization, provided they are soluble in water and that they contain, or are functionalized with, polymerizable groups. The "stable" colloidal state of the resulting nanoparticles is maintained even after freeze drying.

Further, the nanogels and nanoparticles may be effective in cancer treatment. Progress in fundamental cancer biology has not yet been met by a comparable advancement in its clinical treatment. A fundamental reason for this discrepancy is the inability to selectively reach and eliminate tumor tissue with marginal damage to healthy organs, cancer cell targeting by polysaccharide-poloxamer drug delivery systems aims at increasing selectivity and overcoming biological barriers, while transporting higher drug amounts.

Active targeting is accomplished by attachment of specific molecules on the carrier's surface, which enhance the binding and interactions with antigens or receptors expressed on specific cell populations. Targeting ligands explored for cancer therapy include antibodies and antibody fragments which can be conjugated to Polysaccharide-poloxamer for specific active targeted drug delivery.

A major class of chemotherapeutics currently used in clinical practice are the anthracycline molecules. Doxorubicin is probably the most known member of the anthracycline family. These potent anti-proliferative agents are a typical example of drugs whose efficacy is constrained by non-specific toxicities and would therefore benefit by the polysaccharide-poloxamer targeted drug delivery approach.

Immune response and biodegradability issues are a significant concern for drug delivery devices, as well as issues relating to drug targeting and controlled drug release. Consequently, there is an immediate need for a comprehensive answer to these problems. A dextran-poloxamer copolymer nanoparticle (nanogel) offers a universal platform that guarantees a safe, sustained, and controlled drug delivery system.

The thermal response feature of the poloxamer (Pluronic F-127) co-monomer component and the controlled release capability (various ratio compositions of dextran-poloxamer) of polysaccharide-poloxamer nanogels enable development of more effective therapeutic nanoparticles. With continuous advances in identifying new biomarkers and associated targeting ligands it will be increasingly feasible to develop targeted and controlled release nanoparticle products as promising candidates for clinical translation.

Nanoparticles comprised of polysaccharides and poloxamers offer excellent nanocarrier capabilities. Particularly, the Dextran-Pluronic nanogels exhibit ideal characteristics and features desired in a drug delivery system. They are non-oxic, non-immunogenic, non-antigenic, and biodegradable. For targeting, especially, they present a great number of hydroxyl groups for conjugation of prodrugs, enzymes, heavy metals (e.g., Fe) and small molecules, for example.

Example 18: Hydrogel Library Construction

A library of drug loaded nanoparticles is synthesized and characterized as follows. Polymeric nanoparticles are synthesized by an inverse emulsion polymerization approach of Dextran-acrylate and Pluronic-acrylate, which will provide an array of physicochemical properties including size, surface charge, and surface drug loading. Specifically, the nanoparticle library will be synthesized and characterized for nanoparticle physicochemical properties, to identify: (i) particles with diameter of 150-300 nm, (ii) capability of surface conjugation of an antibiotic agent (i.e. polymyxin and vancomycin) and (iii) effective antibiotic (i.e. polymyxin and vancomycin) nanoparticle surface conjugation.

Two commercially available polyoxyethylene-polyoxypropylene block copolymers (Pluronic F-127 and Pluronic F-68) are modified with acrylic groups. Briefly, dried Pluronic F127 (or Pluronic F-68) are dissolved in chloroform in a three-neck flask and cooled to 0° C. After cooling, Triethylamine (TEA) is added to the solution and methacrylic anhydride is added dropwise to the cooled mixture under nitrogen flow with magnetic stirring. The reaction is allowed to proceed for 24 h at 50° C. The crude product is filtered and the filtrate is poured into cold diethyl ether under vigorous stirring for polymer precipitation. The precipitate is filtered, washed twice with pure ether solvent and dried. The structure and molecular weight of Pluronic with methacrylate end-groups can be confirmed by 1H-NMR and gel permeation chromatography (GPC).

Dextran (MW: 40,000) is dissolved in LiCl/DMF (10 Wt. %) mixture solvent system at 90° C. under nitrogen gas purge. After a complete dissolution, the solution is cooled to 70° C. and triethylamine ($Et_3N$) is added dropwise. The dextran solution is stirred vigorously and methacrylic anhydride is then slowly injected into the Dextran/$Et_3N$ with a syringe. The reaction is conducted overnight at 65-70° C. The dextran methacrylate product in the reaction mixture is precipitated in a cold isopropyl alcohol, washed two times with isopropyl alcohol, and dried at room temperature in a vacuum oven. The structure and molecule weight of methacrylated dextran can be confirmed by 1H-NMR and GPC.

Nanogels are synthesized using inverse miniemulsion polymerization of the two presynthesized monomers: (i) MA-DEX, i.e., di-methacrylated dextrane (MW 40,000) and (ii) DMA-F68 (or DMA-F127). In a typical nanoparticle preparation experiment, prepared aqueous solution of methacrylated polymers (deoxygenated solution) is added into Span and Tween 80 Hexane solvent. The mixture is sonicated for 2 min at room temperature using a probe sonicator and opaque white emulsion solution will be obtained. Ammonium persulphate (APS) and tetramethyl ethylene diamine (TMED) in a separate aqueous solution will be immediately added into the emulsion solution to catalyze the polymerization of acrylated monomer solutions into nanogel matrices. The emulsion mixture will be sonicated, and the final translucent solution is left stirring overnight. The hydrogel nanoparticle solution will be centrifuged down and washed twice using Hexane and phosphate buffer and stored in refrigerator for future use. The particle size will be measured using light scattering and transmission electron microscopy (TEM).

Nanogel solution is resuspended in phosphate buffer at pH 7.4 and covered with aluminum foil. Sodium metaperiodate in phosphate buffer at pH 7.4 is added into the nanoparticle solution to oxidize dextran hydroxyl groups into aldehyde groups for drug conjugation. The reaction is carried out at 4° C. for 30 minutes with magnetic stirring. The oxidized nanoparticle are purified by a simple overnight dialysis step protected from light (phosphate buffer, pH 7.4), followed by freeze-drying. The particle size and surface charge will be measured using dynamic light scattering instrument (DLS).

Polymyxin is conjugated onto the oxidized surface of the nanogel using a facile bioconjugation technique. Briefly, Polymyxin in deionized water is added to a photoactive carbohydrate reactive crosslinker azidobenzoylhydrazide (ABH)/DMSO solution and shaken at room temperature for 30 mins. Conjugation of polymyxin and ABH will be furthered completed with UV irradiation for 2 mins. The drug solution is then added into presynthesized nanogel solution and stirred for 2 hour at room temperature in dark conditions. The drug-conjugated nanogel is purified by dialysis in deionized water to remove unconjugated drug molecules, followed by freeze-drying. The particle size and surface charge will be measured using DLS. Vancomycin-conjugated nanogel can be synthesized using a similar method.

Nanoparticle drug loading, degradation, and drug release profiles can be characterized.

Nanogel degradation can be evaluated in terms of fluorescence emitted by either dye molecules attached to the released dextran particles or antibiotics released from the nanoparticle. For example, blue fluorescent dye hydrazide-activated aminomethylcoumarin acetate (AMCA-hydrazide) can be conjugated to nanoparticles. Release studies can be conducted by dialyzing dye/drug containing nanoparticles against 1 L of frequently renewed PBS at pH 7.4 and 37° C. to mimic physiological conditions. The release profile of AMAC dye can be measured in terms of fluorescence using fluorescent spectrophotometry. A standard curve can be constructed by measuring the fluorescence intensities of standards (samples with predetermined concentrations). Fluorescence intensities can be measured for the experimental groups to obtain unknown concentrations. The other alternative is to measure the drug concentration released from the nanoparticles using High Performance Liquid Chromatography (HPLC).

The nanogel degradation and drug release kinetics depend on the extent of acrylate monomer crosslinking. In general, the greater the extent of cross-linking of nanogels, the slower their degradation will be. It is likely that the extent of cross-linking of the nanogel increases with prolonged cross-linking time, resulting in slower in vitro degradation and subsequent release of payload cargo. As such, nanoparticle degradation and drug release profile could be tuned and optimized by adjusting monomer acylation and polymerization degree.

Nanoparticles generally show a poor long-term stability due to the physical instability (aggregation) and/or to the chemical instability (e.g., hydrolysis of polymer materials, drug release from nanoparticles, and chemical reactivity of medicine during the storage), which are frequently noticed when these nanoparticle aqueous suspensions are stored for an extended period. In order to improve the physical and chemical stability of the nanogel, the nanogel formulation can be modified by various parameters such as acrylated dextran and Pluronic polymers ratio, polymer molecular weight, nanoparticle concentration, nanoparticle size, particle surface charge, storage temperature, pH of the aqueous solution, types of surfactants and surfactant concentration. Additionally, the development of freeze dried storage method may maximize the stability of the drug-conjugated nanoparticles and prolong its shelf life. Sugars such as trehalose and sucrose can be used as cryoprotectants to protect the nanoparticles from freezing stress or drying stress (lyoprotectant) and also to increase its stability upon storage.

Figure 5:
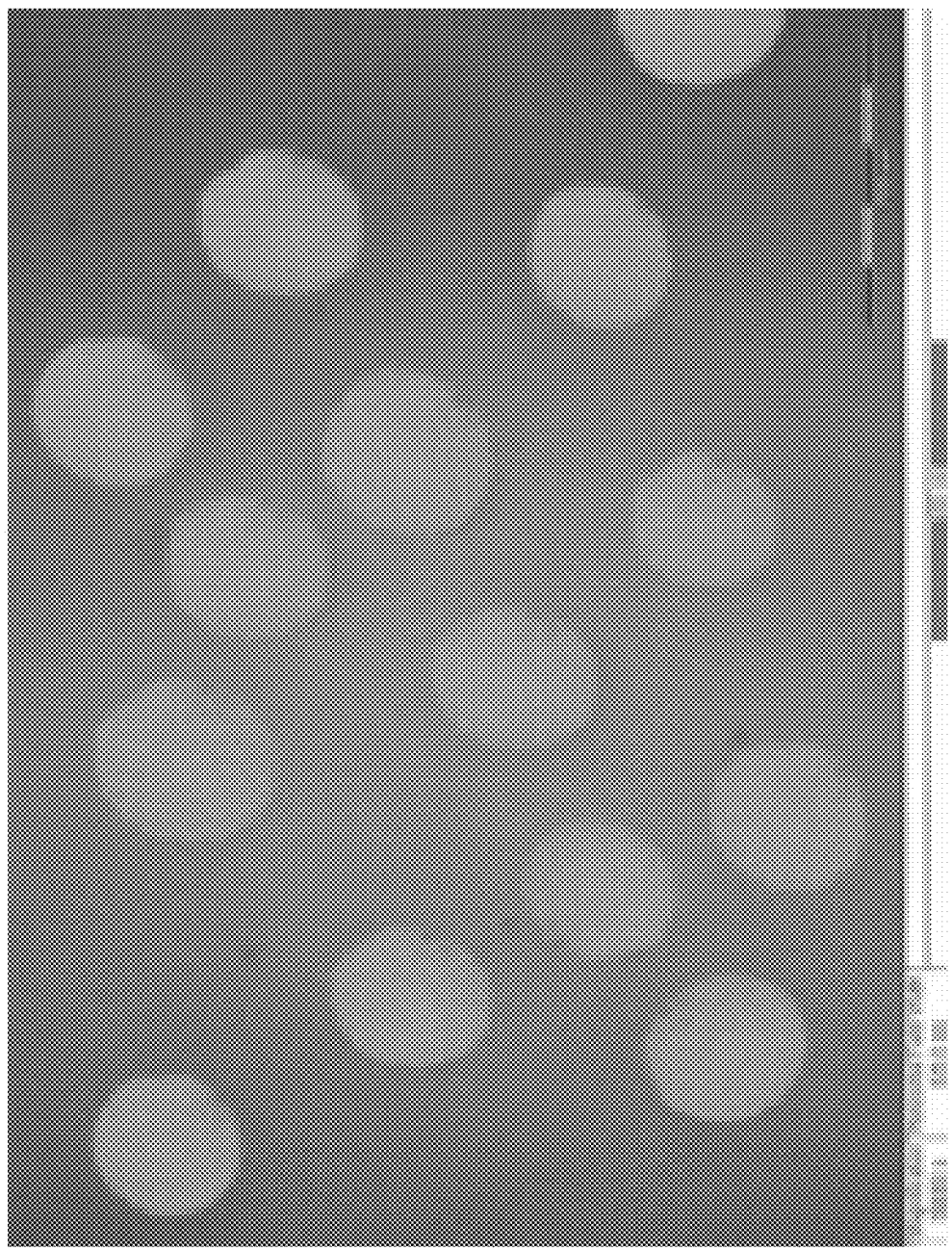
FIG. 5 is a Transmission Electron Micrograph (TEM) showing preparation of nanogel particles (cross-linked dextran and PLURONIC F-127) having a size of about 100 nm (scale bar 200 nm).
Figure 6:
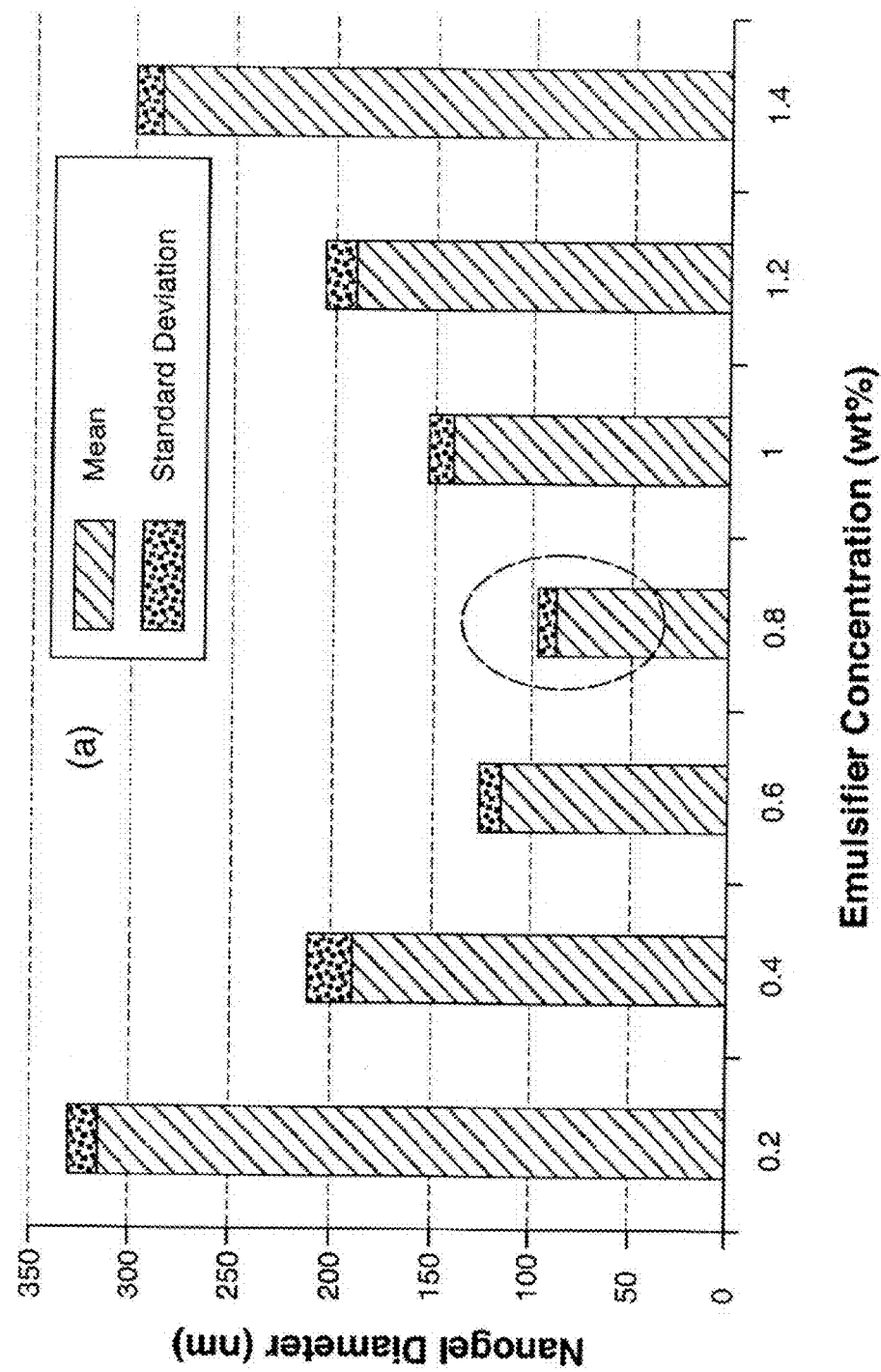
FIG. 6 is a Dynamic Light Scattering Study showing that the nanogel diameter varies with the concentration of an emulsifier (in this case Tween 80). A minimum size of ~90 nm was achieved in this study.

FIG. 5 is a Transmission Electron Micrograph (TEM) showing preparation of nanogel particles (cross-linked dextran and PLURONIC F-127) having a size of about 100 nm (scale bar=200 nm). FIG. 6 is a Dynamic Light Scattering Study showing that the nanogel diameter varies with the concentration of an emulsifier (in this case Tween 80). A minimum size of ~90 nm was achieved in this study.

Example 19: Antimicrobial Activity

Figure 7:
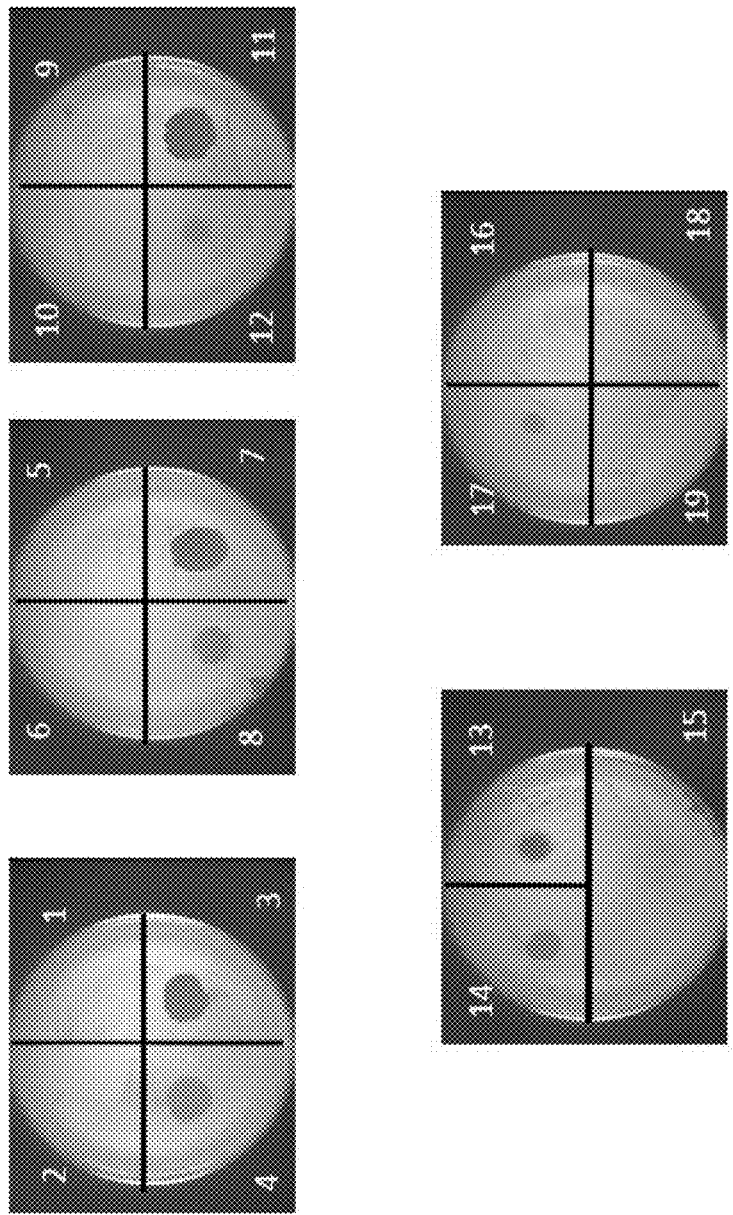
FIG. 7 nanogels conjugated with polymyxin B (PmxnB) or vancomycin (VCM) and/or loaded with 5 mg/nil penicillin/streptomycin (Pen/Strep), and tested on tryptic soy agar for activity against multi-drug resistant (and expanded-spectrum beta-lactamase resistant) *Acinetobacter baumannii* (BAA-1605). (1) unmodified particle, Pen/Strep loaded; (2) unmodified particle; (3) Pen-Strep loaded and conjugated with PmxnB; (4) conjugated with PmxnB; (5) conjugated with VCM, Pen-Strep loaded; (6) conjugated with VCM; (7) conjugated with PmxnB/AMCA, Pen/Strep loaded; (8) conjugated with PmxnB/AMCA (fluorescent agent); (9) conjugated with VCM/AMCA, Pen/Strep loaded; (10) conjugated with VCM/AMCA; (11) PmxnB at 5 mg/ml; (12) VCM at 5 mg/ml; (13) Pen/Strep at 5 mg/ml; (14) PmxnB at 100 µg/ml; (15) VCM at 100 µg/ml; (16) Pen/Strep at 100 µg/ml; (17) PmxnB at 10 µg/ml; (18) VCM at 10 µg/ml; (19) Pen/Strep at 10 µg/ml.
Figure 8:
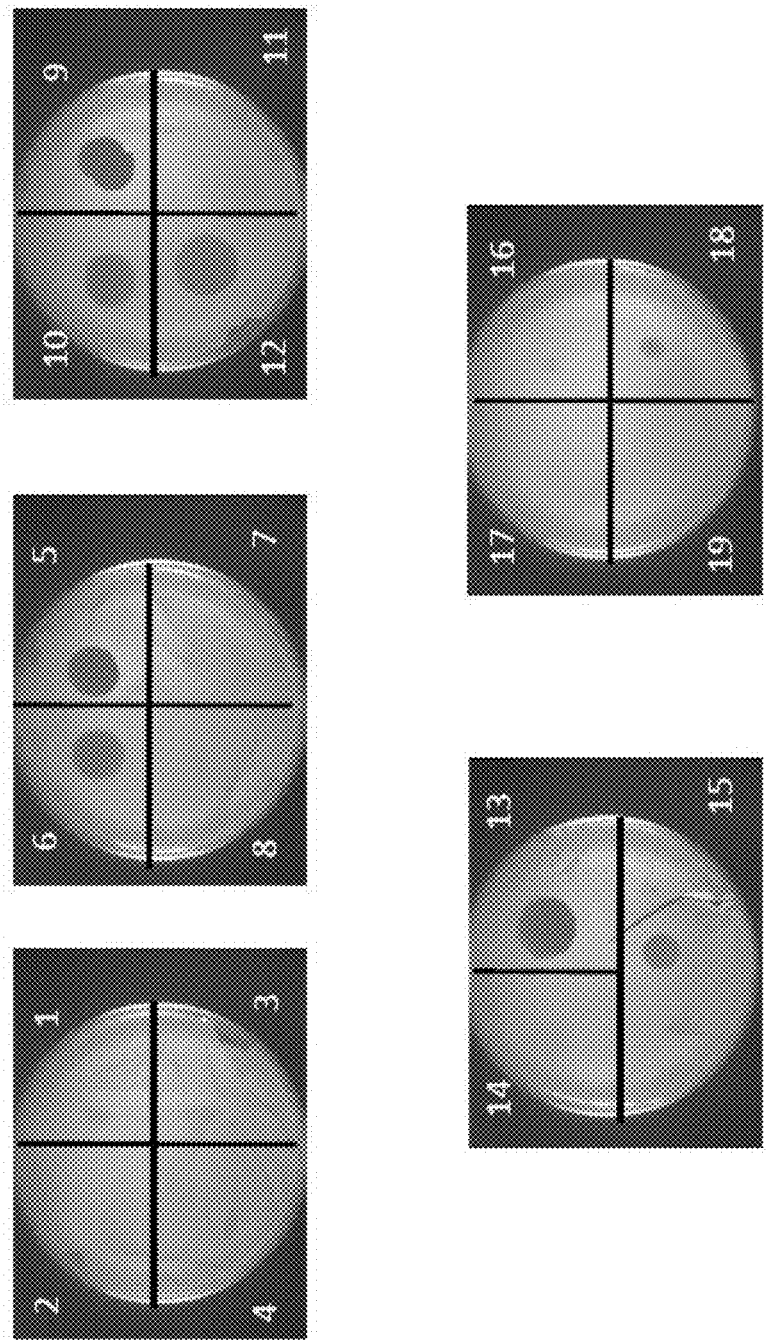
FIG. 8 nanogels conjugated with polymyxin B (PmxnB) or vancomycin (VCM) and/or loaded with 5 mg/ml penicillin/streptomycin (Pen/Strep), and tested on tryptic soy agar for activity against multi-drug resistant (MRSA) *Staphylococcus aureus* (NRS-385). (1) unmodified particle, Pen/Strep loaded; (2) unmodified particle; (3) Pen-Strep loaded and conjugated with PmxnB; (4) conjugated with PmxnB; (5) conjugated with VCM, Pen-Strep loaded; (6) conjugated with VCM; (7) conjugated with PmxnB/AMCA, Pen/Strep loaded; (8) conjugated with PmxnB/AMCA (fluorescent agent); (9) conjugated with VCM/AMCA, Pen/Strep loaded; (10) conjugated with VCM/AMCA; (11) PmxnB at 5 mg/ml; (12) VCM at 5 mg/ml; (13) Pen/Strep at 5 mg/nil; (14) PmxnB at 100 µg/ml; (15) VCM at 100 µg/ml; (16) Pen/Strep at 100 µg/ml; (17) PmxnB at 10 µg/ml; (18) VCM at 10 µg/ml; (19) Pen/Strep at 10 µg/ml.
Figure 9:
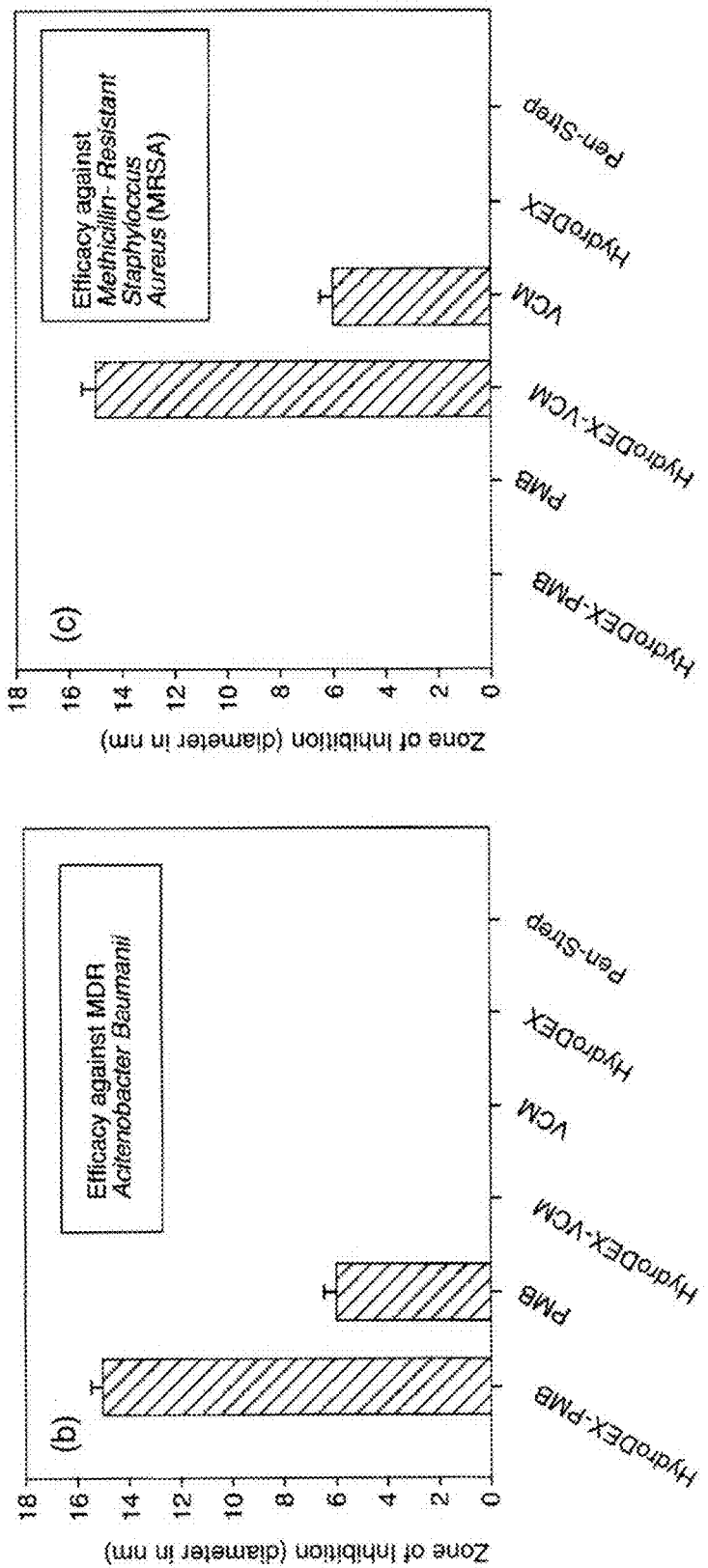
FIG. 9 summarizes the activity against MDR in vitro, as shown in FIGS. 7 and 8. *Acinetobacter baumannii* (a) treated with the hydrogel conjugated with polymyxin B (PMB) produced a clearing zone of ~15 mm in diameter. Free PMB (10 µg/ml) resulted in a clearing zone of ~6 mm against MDR *A. baumannii*. Controls of Vancomycin (VCM)-conjugated particles, free VCM, unconjugated particles, and penicillin/streptomycin (10 µg/ml) resulted in no inhibition. Methicillin-resistant *S. aureus* (MRSA) (b) treated with VCM-conjugated particles produced a clearing zone of ~15 mm in diameter. Free VCM (10 µg/ml) resulted in a clearing zone of ~6 mm against MRSA. Controls of PMB-conjugated particles, free PMB, unconjugated particles, and penicillin/streptomycin at 10 µg/ml resulted in no inhibition.

The concept for targeted killing of bacterial pathogens with the hydrogels of the invention is illustrated in FIG. 1. As shown in FIGS. 7-9, the unmodified particles have no inherent antimicrobial activity. However, conjugating polymyxin B to the nanoparticle surface imparts antimicrobial activity against Gram-negative organisms such as *Acinetobacter baumannii*, but not Gram-positive organisms such as MRSA. Further, conjugating Vancomycin to the nanoparticle surface imparts antimicrobial activity against Gram-positive organisms (i.e. MRSA), but not Gram-negative organisms (i.e. *Acinetobacter baumannii*).

Figure 10:
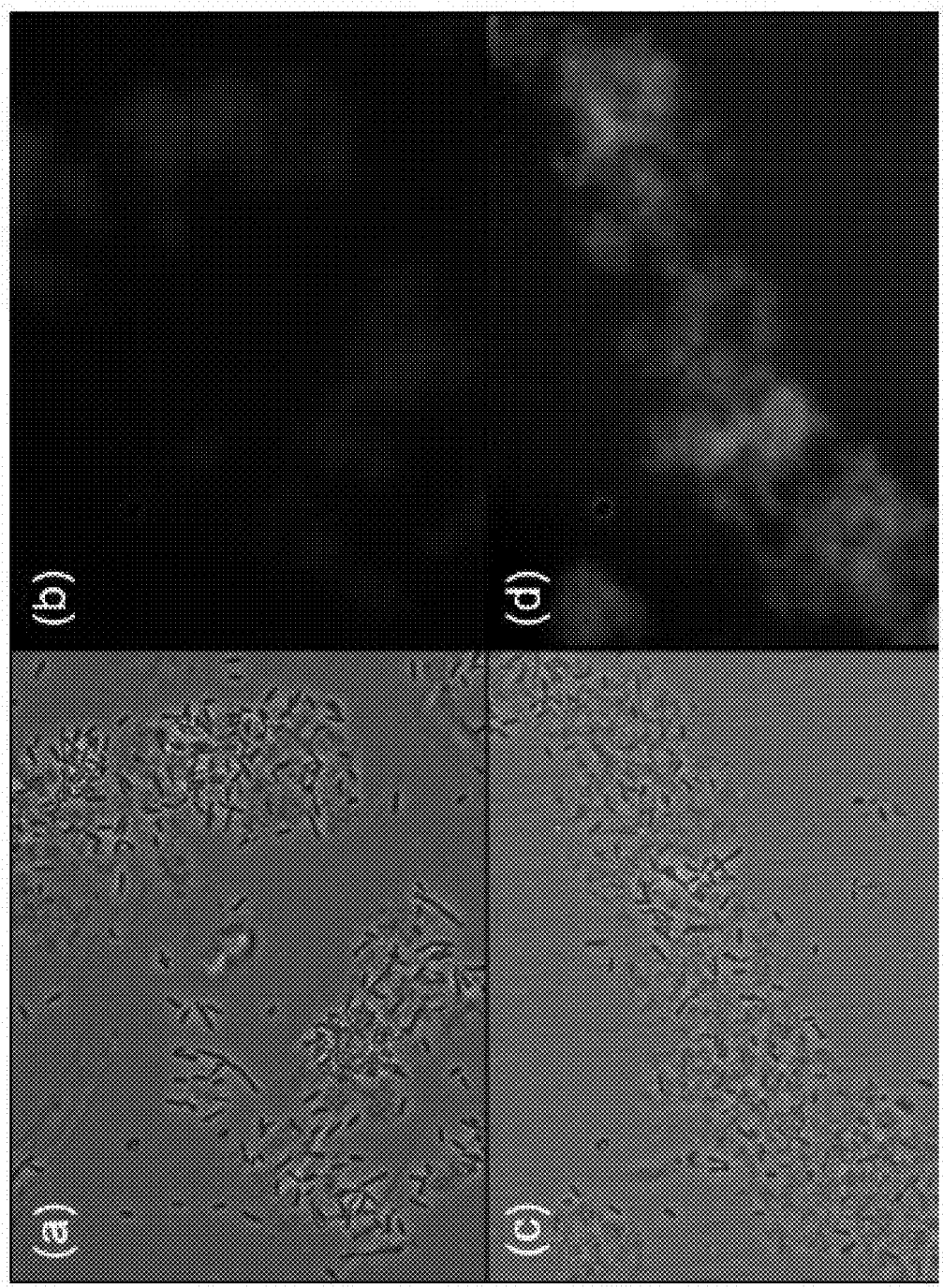
FIG. 10 shows targeting activity of the nanoparticles. Polymyxin B conjugated nanoparticles labeled with fluorophore Aminomethylcoumarin (AMCA) targeting Gram-negative *Escherichia coli* DH5α is shown: (a) bright field image; (b) fluorescent image. Polymyxin B conjugated nanoparticles labeled with fluorophore Aminomethylcoumarin (AMCA) targeting Gram-negative *Pseudomonas aeruginosa* strain 27853: (c) bright field image; (d) fluorescent image.

Conjugating AMCA fluorescent probes to the nanoparticle surface does not negatively impact the killing properties of surface-conjugated polymyxin B or Vancomycin. FIG. 10.

Control Pen/Strep at 5 mg/ml is highly toxic and will kill both Gram-negative and Gram-positive bacteria that have resistance to these antibiotics at clinically relevant levels (i.e. 10 ug/ml) (compare sample 13 to sample 19). Unmodified particles loaded with 5 mg/ml Pen/Strep (i.e. a toxic dose) did not kill bacteria. This can be interpreted two ways. Either much less drug was actually loaded than expected (by an order of magnitude), or the drug load is not released from the nanoparticles when incubated at 37° C. overnight. Either way, the drug load in these experiments was a non-factor and all observed killing is attributable to the surface conjugated polymyxin B or Vancomycin.

Clinically relevant doses (e.g., 10 µg/ml) of control antibiotics confirmed MRSA is resistant to polymyxin B but sensitive to Vancomycin, *A. baumannii* is resistant to Vancomycin but sensitive to polymyxin B, and both strains are resistant to Pen/Strep, confirming their multi-drug resistant label.

Figure 11:
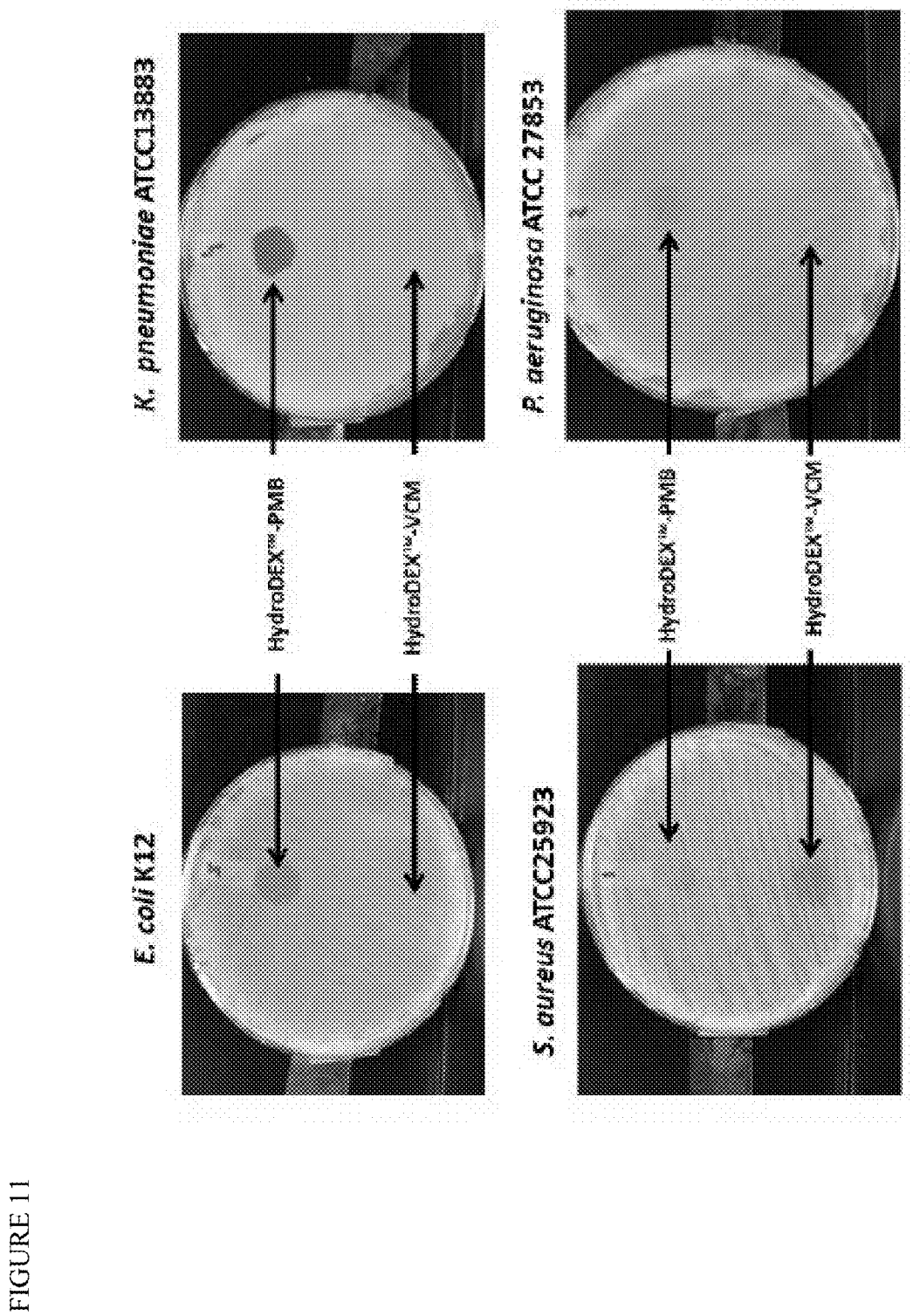
FIG. 11 shows antimicrobial testing against clinical isolates: *E. coli* K12, *K. pneumoniae* ATCC 13883, *S. aureus* ATCC 25923, and *P. aeruginosa* ATCC 27853.

FIG. 11 shows antimicrobial testing against clinical isolates: *E. coli* K12, *K. pneumoniae* ATCC 13883, *S. aureus* ATCC 25923, and *P. aeruginosa* ATCC 27853.

The invention claimed is:

1. A hydrogel composition, comprising:
   a population of cross-linked polymeric nanoparticles having conjugated to their surface polymyxin B and vancomycin, wherein the cross-linked polymeric nanoparticles comprise at least one cross-linked polysaccharide polymer.

2. The hydrogel composition of claim 1, wherein the nanoparticles comprise cross-linked copolymers.

3. The hydrogel composition of claim 2, wherein at least one co-polymer is a polysaccharide, which is either linear, cyclic or branched.

4. The hydrogel composition of claim 3, wherein the polysaccharide is a glucan.

5. The hydrogel composition of claim 3, wherein the polysaccharide is at least one of dextran, chitosan, and cyclodextran.

6. The hydrogel composition of claim 2, wherein at least one co-polymer is selected from polyvinyl alcohol, acrylate, and polyacrylate.

* * * * *